(12) United States Patent
Mao et al.

(10) Patent No.: US 12,141,965 B2
(45) Date of Patent: Nov. 12, 2024

(54) SYSTEMS AND METHODS FOR IMAGE QUALITY OPTIMIZATION

(71) Applicant: SHANGHAI UNITED IMAGING HEALTHCARE CO., LTD., Shanghai (CN)

(72) Inventors: Yifu Mao, Shanghai (CN); Liyi Zhao, Shanghai (CN); Wenjing Cao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 581 days.

(21) Appl. No.: 17/446,303

(22) Filed: Aug. 30, 2021

(65) Prior Publication Data

US 2021/0390694 A1    Dec. 16, 2021

Related U.S. Application Data

(63) Continuation of application No. PCT/CN2021/094461, filed on May 18, 2021.

(30) Foreign Application Priority Data

Jan. 13, 2021    (CN) ......................... 202110044133.9

(51) Int. Cl.
*G06T 7/12* (2017.01)
*G06T 5/50* (2006.01)
(Continued)

(52) U.S. Cl.
CPC .............. *G06T 7/0012* (2013.01); *G06T 5/50* (2013.01); *G06T 5/70* (2024.01); *G06T 5/73* (2024.01);
(Continued)

(58) Field of Classification Search
CPC ........... G06T 7/0012; G06T 5/50; G06T 5/70; G06T 5/73; G06T 5/90;
(Continued)

(56) References Cited

U.S. PATENT DOCUMENTS

| 4,456,926 A | 6/1984 | Kruger et al. |
|---|---|---|
| 2004/0068167 A1 | 4/2004 | Hsieh et al. |

(Continued)

FOREIGN PATENT DOCUMENTS

| CA | 2455088 A1 | 8/2004 |
|---|---|---|
| CN | 101156780 A | 4/2008 |

(Continued)

OTHER PUBLICATIONS

The Extended European Search Report in European Application No. 21808874.8 mailed on Sep. 13, 2023, 8 pages.
(Continued)

*Primary Examiner* — Charlotte M Baker
(74) *Attorney, Agent, or Firm* — METIS IP LLC

(57) ABSTRACT

The present disclosure discloses methods and systems for image quality optimization. The method may include obtaining an image to be processed. The method may also include determining at least one related feature of the image. The at least one related feature may include at least one of an acquisition parameter feature relating to the image, an imaging parameter feature relating to the image, an imaging subject feature of an imaging subject, or a quality feature of the image. The method may also include inputting the image and the at least one related feature into an image processing model. The method may also include determining an optimized image of the image based on an output of the image processing model.

20 Claims, 15 Drawing Sheets

(51) Int. Cl.
  *G06T 5/70* (2024.01)
  *G06T 5/73* (2024.01)
  *G06T 5/90* (2024.01)
  *G06T 7/00* (2017.01)
  *G16H 30/40* (2018.01)
  *G16H 50/20* (2018.01)

(52) U.S. Cl.
  CPC ............... *G06T 5/90* (2024.01); *G16H 30/40* (2018.01); *G16H 50/20* (2018.01); *G06T 2207/10116* (2013.01); *G06T 2207/20081* (2013.01); *G06T 2207/20084* (2013.01); *G06T 2207/20182* (2013.01); *G06T 2207/30004* (2013.01); *G06T 2207/30168* (2013.01)

(58) Field of Classification Search
  CPC . G06T 2207/10116; G06T 2207/20081; G06T 2207/20084; G06T 2207/20182; G06T 2207/30004; G06T 2207/30168; G06T 5/60; G06T 2210/41; G06T 11/008; G06T 2207/10081; G16H 30/40; G16H 50/20
  USPC .......................................................... 382/128
  See application file for complete search history.

(56) References Cited

U.S. PATENT DOCUMENTS

| | | | |
|---|---|---|---|
| 2008/0108895 A1 | 5/2008 | Sabol et al. |
| 2014/0152800 A1 | 6/2014 | Fomitchov et al. |
| 2014/0307847 A1 | 10/2014 | Schmidt et al. |
| 2014/0369577 A1 | 12/2014 | Collins et al. |
| 2015/0359501 A1 | 12/2015 | Eronen et al. |
| 2017/0103512 A1 | 4/2017 | Mailhe et al. |
| 2017/0143312 A1 | 5/2017 | Hedlund et al. |
| 2017/0337713 A1 | 11/2017 | Hoelzer et al. |
| 2017/0372193 A1 | 12/2017 | Mailhe et al. |
| 2020/0027251 A1 | 1/2020 | Demesmaeker et al. |
| 2020/0043204 A1 | 2/2020 | Fu et al. |
| 2020/0104711 A1 | 4/2020 | Aytekin et al. |
| 2020/0126231 A1 | 4/2020 | Hu et al. |
| 2020/0372682 A1* | 11/2020 | Kim ...................... G06N 3/084 |
| 2020/0380737 A1 | 12/2020 | Bao et al. |
| 2021/0248765 A1 | 8/2021 | Zhang et al. |

FOREIGN PATENT DOCUMENTS

| | | |
|---|---|---|
| CN | 104318524 A | 1/2015 |
| CN | 106485680 A | 3/2017 |
| CN | 106952239 A | 7/2017 |
| CN | 107301662 A | 10/2017 |
| CN | 107341516 A | 11/2017 |
| CN | 108881708 A | 11/2018 |
| CN | 109242788 A | 1/2019 |
| CN | 110151210 A | 8/2019 |
| CN | 110490118 A | 11/2019 |
| CN | 110610463 A | 12/2019 |
| CN | 110660123 A | 1/2020 |
| CN | 110853742 A | 2/2020 |
| CN | 111612867 A | 9/2020 |
| EP | 3485815 A1 | 5/2019 |
| WO | 2019033390 A1 | 2/2019 |
| WO | 2019114027 A1 | 6/2019 |

OTHER PUBLICATIONS

The Extended European Search Report in European Application No. 20936697.0 mailed on Jan. 16, 2023, 9 pages.

International Search Report in PCT/CN2020/090862 mailed on Feb. 20, 2021, 4 pages.

Written Opinion in PCT/CN2020/090862 mailed on Feb. 19, 2021, 4 pages.

Yan, Qiujuan, System Conststcfion and Optimization of Imaging Quality for Photon Counting Detector, Master's Electronic Journal, 2020, 72 pages.

\* cited by examiner

700

```
Obtaining a plurality of training samples     710
and a plurality of standard images
corresponding to the plurality of training
samples respectively
              |
              v
Generating an image processing model          720
by training a preliminary image
processing model based on the plurality
of training samples and the plurality of
standard images
```

Obtaining a plurality of qualified images relating to a subject type ~1110

Generating a plurality of sample images by preprocessing the plurality of qualified images ~1120

Generating an image processing model corresponding to the subject type by training a preliminary image processing model based on the plurality of sample images and a plurality of sample quality features corresponding to the plurality of sample images ~1130

FIG. 11

SYSTEMS AND METHODS FOR IMAGE QUALITY OPTIMIZATION

CROSS-REFERENCE TO RELATED APPLICATIONS

This application is a continuation of International Application No. PCT/CN2021/094461, filed on May 18, 2021, which claims priority to Chinese Patent Application No. 202110044133.9, filed on Jan. 13, 2021, which claims priority to International Application No. PCT/CN2020/090862, filed on May 18, 2020, the content of each of which is hereby incorporated by reference.

TECHNICAL FIELD

The present disclosure generally relates to image processing, and more particularly, relates to systems and methods for image quality optimization.

BACKGROUND

With the development of medical imaging technology, image quality optimization, such as image denoising and/or artifact decreasing, etc., has become more and more important in the process of medical image processing. At present, machine learning techniques may be applied to image quality optimization. However, traditional machine learning techniques can't achieve relatively good optimization results. Therefore, it is desirable to provide systems and methods for image quality optimization to improve performances of machine learning models in denoising, artifact reducing, motion correction, and/or resolution increasing, thereby improving effectiveness of medical image processing.

SUMMARY

According to one aspect of the present disclosure, a method for image quality optimization is provided. The method may include obtaining an image to be processed and determining at least one related feature of the image. The at least one related feature may include at least one of an acquisition parameter feature relating to the image, an imaging parameter feature relating to the image, an imaging subject feature of an imaging subject, or a quality feature of the image. The method may also include inputting the image and the at least one related feature into an image processing model. The method may also include determining an optimized image corresponding to the image based on an output of the image processing model.

According to another aspect of the present disclosure, a method for image quality optimization is provided. The method may include obtaining acquisition data to be processed, and determining at least one related feature of the acquisition data. The at least one related feature may include at least one of an acquisition parameter feature relating to the acquisition data, an imaging subject feature of an imaging subject, or a quality feature of the acquisition data. The method may also include inputting the acquisition data and the at least one related feature into an image processing model and determining an optimized image corresponding to the acquisition data based on an output of the image processing model.

According to another aspect of the present disclosure, a system for image quality optimization is provided. The system may include an acquisition module, a determination module, an inputting module, and an optimization module. The acquisition module may be configured to obtain an image to be processed. The determination module may be configured to determine at least one related feature of the image. The at least one related feature may include at least one of an acquisition parameter feature relating to the image, an imaging parameter feature relating to the image, an imaging subject feature of an imaging subject, or a quality feature of the image. The inputting module may be configured to input the image and the at least one related feature into an image processing model. The optimization module may be configured to determine an optimized image corresponding to the image based on an output of the image processing model.

According to another aspect of the present disclosure, a system for image quality optimization is provided. The system may include an acquisition module, a determination module, an inputting module, and an optimization module. The acquisition module may be configured to obtain acquisition data to be optimized. The determination module may be configured to determine at least one related feature of the acquisition data. The at least one related feature may include at least one of an acquisition parameter feature relating to the acquisition data, an imaging subject feature of an imaging subject, or a quality feature of the acquisition data. The inputting module may be configured to input the acquisition data and the at least one related feature into an image processing model. The optimization module may be configured to determine optimized image data corresponding to the acquisition data based on an output of the image processing model.

According to another aspect of the present disclosure, a device for image quality optimization is provided. The device may include a processor and a storage device including a set of instructions. When executed by the processor, the set of instructions may direct the processor to execute operations corresponding to the abovementioned image quality optimization method.

According to still another aspect of the present disclosure, a computer-readable storage medium including computer instructions is provided. When executed by a processor, the computer instructions may direct the processor to execute operations corresponding to the abovementioned image quality optimization method.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 7 is a flowchart illustrating an exemplary process for training an image processing model according to some embodiments of the present disclosure;

FIG. 11 is a flowchart illustrating an exemplary process for obtaining an image processing model corresponding to a subject type according to some embodiments of the present disclosure;

DETAILED DESCRIPTION

Figure 1:
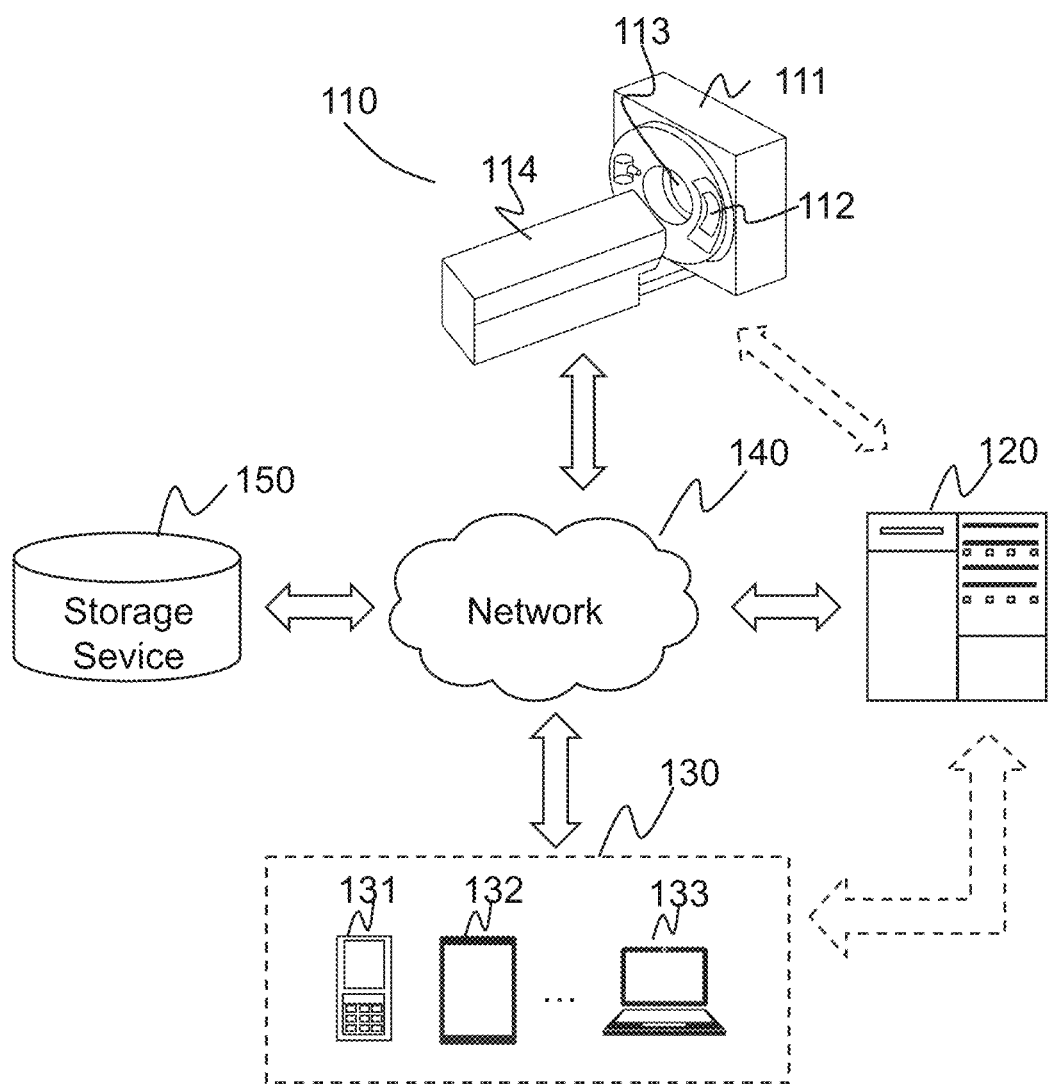
FIG. 1 is a schematic diagram illustrating an exemplary imaging quality optimization system according to some embodiments of the present disclosure.

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It will be understood that the term "system," "device," "unit," and/or "module" used herein are one method to distinguish different components, elements, parts, section or assembly of different level in ascending order. However, if other words may achieve the same purpose, the words may be replaced by other expressions.

As used in the disclosure and the appended claims, the singular forms "a," "an," and "the" include plural referents unless the content clearly dictates otherwise. In general, the terms "comprise" and "include" merely prompt to include steps and elements that have been clearly identified, and these steps and elements do not constitute an exclusive listing. The methods or devices may also include other steps or elements.

The flowcharts used in the present disclosure illustrate operations that systems implement according to some embodiments of the present disclosure. It should be noted that the foregoing or the following operations may not be performed in the order accurately. Instead, the steps may be processed in reverse order or simultaneously. Moreover, other operations may also be added into these procedures, or one or more steps may be removed from these procedures.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging/treatment, such as for disease diagnostic, disease therapy, or research purposes. In some embodiments, the systems may include an imaging system. The imaging system may include a single modality imaging system and/or a multi-modality imaging system. The term "modality" used herein broadly refers to an imaging or treatment method or technology that gathers, generates, processes, and/or analyzes imaging information of a subject or treatments the subject. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (N IRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc. It should be noted that the medical system described below is merely provided for illustration purposes, and not intended to limit the scope of the present disclosure.

In the present disclosure, a subject may include a biological subject and/or a non-biological subject. The biological subject may be a human being, an animal, a plant, or a specific portion, organ, and/or tissue thereof. For example, the subject may include a head, a neck, a thorax, a heart, a stomach, a blood vessel, a soft tissue, a tumor, a nodule, or the like, or any combination thereof. In some embodiments, the subject may be a man-made composition of organic and/or inorganic matters that are with or without life. In the present disclosure, when the subject represents a human being, an animal, a plant, or a specific portion thereof, the terms "imaging subject" and "subject" can be used interchangeably. When the subject represents an organ and/or a tissue, the term "imaging target" and "subject" can be used interchangeably.

In the present disclosure, a representation of a subject (e.g., a patient, an object, or a portion thereof) in an image may be referred to as "subject" for brevity. For example, a representation of an organ and/or tissue (e.g., a heart, a liver, a lung) in an image may be referred to as an organ or tissue for brevity. Further, an image including a representation of a subject may be referred to as an image of a subject or an image including a subject for brevity. Still further, an operation performed on a representation of a subject in an image may be referred to as an operation performed on a subject for brevity. For instance, a segmentation of a portion of an image including a representation of an organ or tissue from the image may be referred to as a segmentation of an organ or tissue for brevity.

FIG. 1 is a schematic diagram of an exemplary image quality optimization system according to some embodiments of the present disclosure.

As shown in FIG. 1, the image quality optimization system 100 may include an imaging device 110, a processing device 120, a terminal device 130, a network 140, and a storage device 150. The connection among the components of the image quality optimization system 100 may be variable. For example, the imaging device 110 may be connected to the processing device 120 through the network 140, or may be connected to the processing device 120 directly (as illustrated by dashed arrow connecting the imaging device 110 and the processing device 120 shown in FIG. 1). As another example, the storage device 150 may be connected to the processing device 120 directly or via the network 140. As a further example, the terminal device 130 may be connected to the processing device 120 through the network 140, or may be connected to the processing device 120 directly (as illustrated by dashed arrow connecting the terminal device 130 and the processing device 120 shown in FIG. 1).

The imaging device 110 may scan an imaging subject located within a scan area (also referred to as "imaging area") and generate imaging data (also referred to as "raw data" or "scanning data") related to the imaging subject. The imaging subject may include a biological subject (e.g., a human body, an animal), a non-biological subject (e.g., a phantom), etc. In some embodiments, the imaging device 110 may be a computed tomography (CT) imaging device, a positive electron emission computed tomography (PET) imaging device, a magnetic resonance imaging (MRI) device, a single photon emission computed tomography (SPECT) imaging device, an emission computed tomography (ECT) imaging device, an ultrasound imaging (UI) device, a digital radiography (DR) imaging device, or the like, or any combination thereof (e.g., a PET-CT device, a PET-MRI imaging device).

In some embodiments, the imaging device 110 may include a gantry 111, a detector 112, an imaging region 113, and a table 114. The gantry 111 may support the detector 112. The imaging subject may be placed on the table 114 and moved into the imaging region 113 to accept a scan. In some embodiments, the detector 112 may include one or more detector units. The detector units may include a single row detector and/or a multi-row detector. The detector unit may include a scintillation detector (e.g., a cesium iodide detector) or other detectors. In some embodiments, the gantry 111 may rotate clockwise or counterclockwise around a rotating axis of the gantry 111. In some embodiments, the imaging device 110 may further include an X-ray tube (not shown) which may be rotated with the gantry 111. The X-ray tube may emit radiation beams (e.g., X-rays) to the imaging subject, which can be detected by the detector 112 after being attenuated by the imaging subject, thereby generating the imaging data.

The processing device 120 may process data and/or information acquired from the imaging device 110, the terminal device 130, and/or the storage device 150. For example, the processing device 120 may generate an image based on imaging data acquired by the imaging device 110. As another example, the processing device 120 may perform a quality optimization process on the generated image. Specifically, the processing device 120 may determine at least one related feature relating to an image. The at least one related feature may include an acquisition parameter feature relating to the image, an imaging parameter feature relating to the image, an imaging subject feature of the imaging subject, a quality feature of the image, or the like, or any combination thereof. The processing device 120 may input the image and the at least one related feature into an image processing model. The processing device 120 may determine an optimized image corresponding to the image based on an output of the image processing model. In some embodiments, the processing device 120 may be a single server or a server group. The server group may be a centralized or distributed. In some embodiments, the processing device 120 may be local or remote.

The terminal device 130 may include a mobile device 131, a tablet computer 132, a laptop computer 133, or the like, or any combination thereof. In some embodiments, the terminal device 130 may interact with other components of the image quality optimization system 100 via the network 140. For example, the terminal device 130 may transmit one or more control instructions to the imaging device 110 to control the imaging device 110 to scan the imaging subject according to the instructions. In some embodiments, the mobile device 131 may include, but not limited to, a smartphone, a handheld gaming device, smart glasses, a smart watch, a wearable device, a virtual display device, an augmented display device, or the like, or any combination thereof. In some embodiments, the terminal device 130 may be part of the processing device 120. In some embodiments, the terminal device 130 may be integrated with the processing device 120 as a console of the imaging device 110. For example, a user/operator (e.g., a doctor) of the image quality optimization system 100 may control an operation of the imaging device 110, for example, scanning the imaging subject.

The network 140 may include any suitable network that can facilitate the exchange of information and/or data for the image quality optimization system 100. For example, the network 140 may include a wired network, a fiber-optic network, a telecommunications network, a local area network, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 140 may include one or more network access points. For example, the network 140 may include wired and/or wireless network access points such as base stations and/or Internet exchange points through which one or more components of the image quality optimization system 100 may be connected to the network 140 to exchange data and/or information.

The storage device 150 may store data (e.g., the scanning data of the imaging subject), instructions, and/or any other information. In some embodiments, the storage device 150 may store data acquired from the imaging device 110, the terminal device 130, and/or processing device 120. For example, the storage device 150 may store a treatment plan, the scanning data of the imaging subject, etc., obtained from the imaging device 110. In some embodiments, the storage device 150 may store data and/or instructions that the processing device 120 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 150 may be implemented on a cloud platform. For example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 140 to communicate with one or more other components (e.g., the processing device 120, the terminal device 130) of the image quality optimization system 100. One or more components of the image quality optimization system 100 may access the data or instructions stored in the storage device 150 via the network 140. In some embodiments, the storage device 150 may be part of the processing device 120, or may be independent that is directly or indirectly connected to the processing device 120.

It should be noted that the above description regarding the image quality optimization system 100 is merely provided for the purposes of illustration, and not intended to limit the scope of the present disclosure. For persons having ordinary skills in the art, multiple variations and modifications may be made under the teachings of the present disclosure. For example, the image quality optimization system 100 may include one or more additional components and/or one or more components of the image quality optimization system 100 may be omitted. Additionally or alternatively, two or more components of the image quality optimization system 100 may be integrated into a single component. A component of the image quality optimization system 100 may be implemented on two or more subcomponents.

Figure 2:
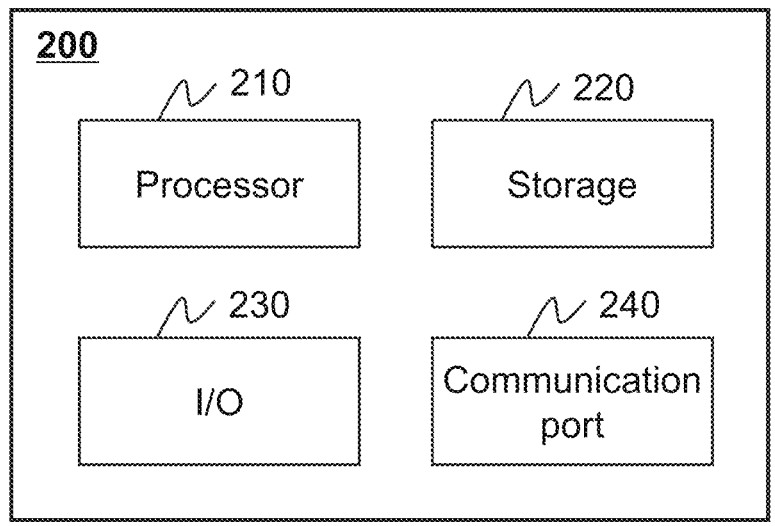
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. The computing device 200 may be used to implement any components of the image quality optimization system 100 as described herein. For example, the processing device 120 and/or the terminal device 130 may be implemented on the computing device 200, respectively via its hardware, software program, firmware, or a combination thereof. Although only one such computing device is shown for convenience, the computer functions relating to the image quality optimization system 100 described herein may be implemented in a distributed manner on multiple similar platforms, to distribute the processing load. As shown in FIG. 2, the computing device 200 may include a processor 210, a storage 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, subjects, components, data structures, processes, modules, and functions, which perform particular functions described herein. For example, the processor 210 may execute instructions obtained from the terminal device 130 and/or the storage device 150. In some embodiments, the processor 210 may include one or more hardware processors, such as a microcontroller, a microprocessor, a reduced instruction set computer (RISC), an application specific integrated circuit (ASIC), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the processing device 120, the storage device 150, the terminal device 130, and/or any other component of the image quality optimization system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input and/or output signals, data, information, etc. In some embodiments, the I/O 230 may enable a user interaction with the processing device 120. In some embodiments, the I/O 230 may include an input device and an output device. Exemplary input devices may include a keyboard, a mouse, a touch screen, a microphone, or the like, or any combination thereof. Exemplary output devices may include a display device, a speaker, a printer, a projector, or the like, or any combination thereof. Exemplary display devices may include a liquid crystal display (LCD), a light-emitting diode (LED)-based display, a flat panel display, a curved screen, a television device, a cathode ray tube (CRT), a touch screen, or the like, or any combination thereof.

The communication port 240 may be connected to a network (e.g., the network 140) to facilitate data communication. The communication port 240 may establish connections between the processing device 120 and the imaging device 110, the terminal device 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed port. For example, the communication port 240 may be designed in accordance with the medical digital imaging and communications in medicine (DICOM) protocol.

Figure 3:
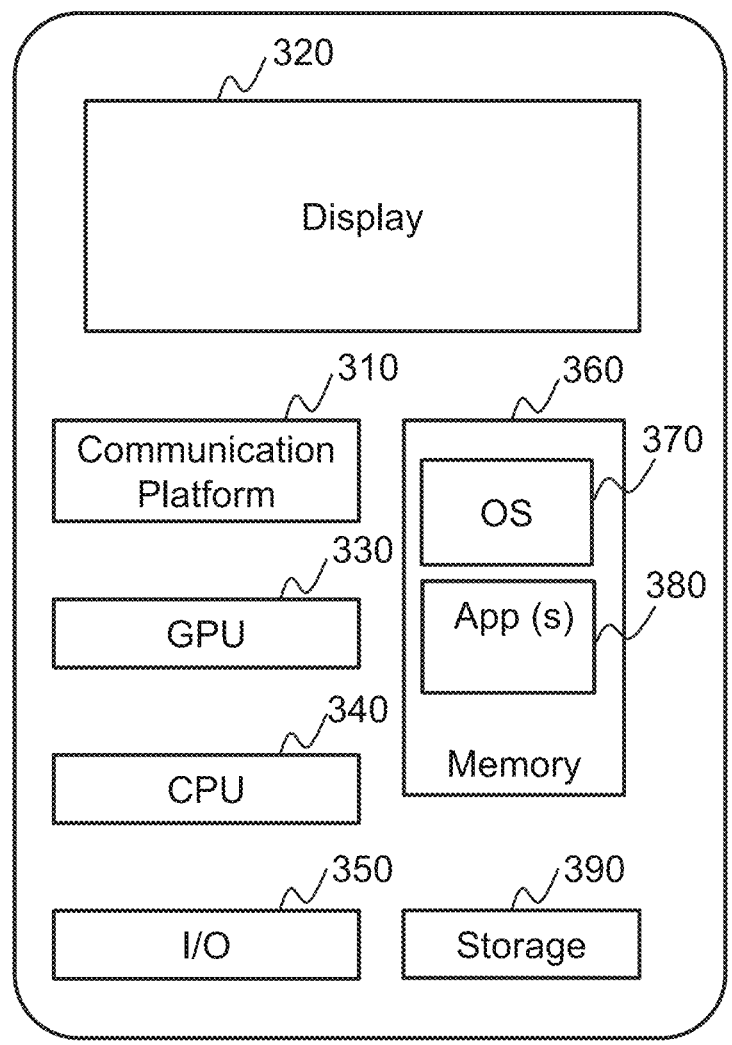
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components of the image quality optimization system 100 (e.g., the terminal device 130 and/or the processing device 120) may be implemented on the mobile device 300.

As shown in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™), and one or more application 380 may be loaded into the memory 360 from the storage 390 in order to be executed by the CPU 340. The applications 380 may include a browser or any other suitable mobile application for receiving and rendering information or other information related to image processing from the processing device 120. User interaction with the information stream may be achieved by the I/O 350 and provided to the processing device 120 and/or other components of the image quality optimization system 100 via network 140.

To implement various modules, units, and their functionalities described in the present disclosure, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
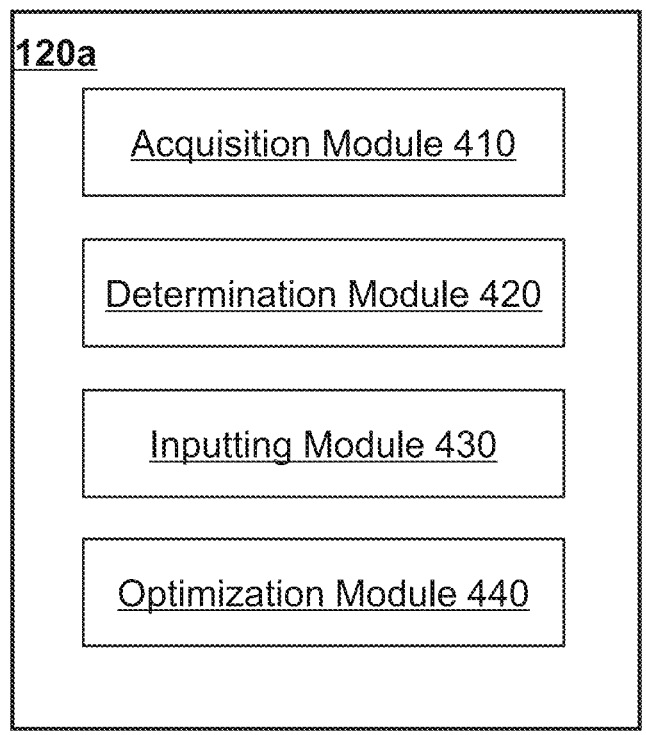
FIG. 4A and FIG. 4B are block diagrams illustrating exemplary processing devices according to some embodiments of the present disclosure.
Figure 4B:
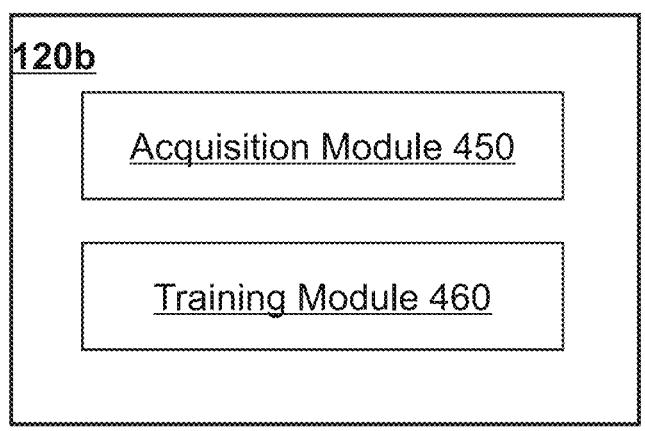

FIG. 4A and FIG. 4B are block diagrams illustrating exemplary processing devices according to some embodiments of the present disclosure.

In some embodiments, as described in FIG. 1, the processing device 120a and the processing device 120b may be embodiments of the processing device 120. In some embodiments, the processing device 120a and the processing device 120b may be implemented on a same device or separated devices. For example, the processing device 120a and processing device 120b may be implemented on the computing device 200. As another example, the processing device 120a may be implemented on the mobile device 300, and the processing device 120b may be implemented on the computing device 200.

Modules in the processing device 120a and/or the processing device 120b may be connected or communicated with each other by a wired or wireless connection.

As shown in FIG. 4A, the processing device 120a may include an acquisition module 410, a determination module 420, an inputting module 430, and an optimization module 440.

The acquisition module 410 may be configured to acquire data and/or information from one or more components of the image quality optimization system 100. For example, the acquisition module 410 may be used to acquire an image to be processed from a storage device or a terminal device described elsewhere in the present disclosure. The image to be processed may refer to an image (e.g., a 2D image, a 3D image, a 4D image) or raw image data (e.g., raw CT data acquired by the imaging device 110). As another example, the acquisition module 410 may acquire an image processing model from a storage device as described elsewhere in the present disclosure. The image processing model may be a machine learning model (e.g., a deep learning model). In some embodiments, the acquisition module 410 may select the image processing model based on related features of the image, a type of an imaging device (also referred to as "imaging device type"), a type of a reconstruction algorithm, a type of an imaging subject (also referred to as "imaging subject type"), a type of an imaging target (also referred to as "imaging target type"), or an optimization purpose. More descriptions regarding the image and the image processing model may be found elsewhere in the present disclosure, for example, operations 510 and 530 and the descriptions thereof.

The determination module 420 may be configured to determine at least one related feature of the image. The at least one related feature may include an acquisition parameter feature relating to the image, an imaging parameter feature relating to the image, an imaging subject feature of the imaging subject, a quality feature of the image, or the like, or any combination thereof. In some embodiments, the determination module 420 may determine the quality feature based on an optimization purpose (e.g., reducing noise, reducing artifact, increasing resolution, increasing contrast, reducing motion). More descriptions regarding the related features may be found elsewhere in the present disclosure, for example, operation 520 and the descriptions thereof.

The inputting module 430 may be configured to input data to be processed into the image processing model. For example, the inputting module 430 may be used to input the image and the at least one related feature into the image processing model. In some embodiments, the inputting module 430 may preprocess the image and input the preprocessed image and the related feature into the image processing model.

The optimization module 440 may be configured to determine an optimized image corresponding to the image based on an output of the image processing model. In some embodiments, the optimization module 440 may perform a post-processing operation on the output of the image processing model to determine the optimized image.

More descriptions regarding the determination of the optimized image may be found elsewhere in the present disclosure, for example, operations 530 and 540 and the descriptions thereof.

As shown in FIG. 4B, the processing device 120*b* may include an acquisition module 450 and a training module 460.

The acquisition module 450 may be configured to acquire data and/or information from one or more components of the image quality optimization system 100. For example, the acquisition module 450 may acquire a plurality of training samples and corresponding standard images from a storage device described elsewhere in the present disclosure. For example, the acquisition module 450 may acquire a plurality of qualified images from a storage device described elsewhere in the present disclosure. The acquisition module 410 may preprocess the plurality of qualified images to generate the plurality of training samples.

The training module 460 may be configured to generate an image processing model based on a training process. In some embodiments, the training module 460 may train a preliminary image processing model based on the plurality of training samples. For example, the training module 460 may train the preliminary image processing model through an iterative process until a termination condition is satisfied. The image processing model may be determined in response to that the termination condition is satisfied. In some embodiments, the termination condition may be related to a value of a loss function. The loss function may be positively correlated with a quality weight, and the quality weight may be related to the quality feature of the sample image. Different training samples may correspond to different quality weights.

Figure 8:
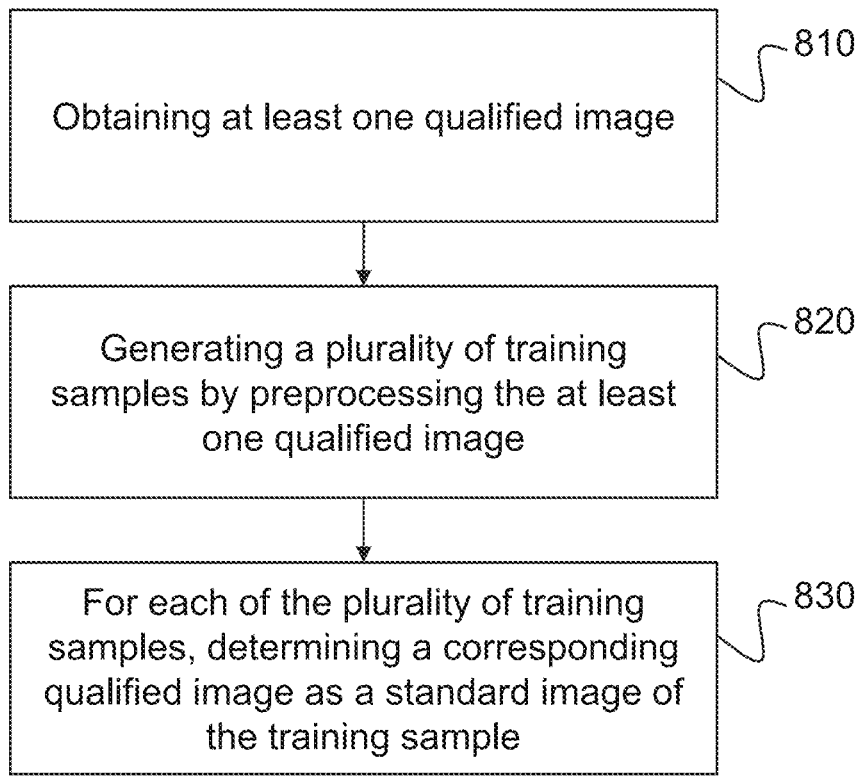
FIG. 8 is a flowchart illustrating an exemplary process for obtaining a plurality of training samples according to some embodiments of the present disclosure.

More descriptions regarding the generation of the imaging processing model through the training may be found elsewhere in the present disclosure, for example, FIGS. 7 and 8 and the descriptions thereof.

It should be understood that the modules shown in FIGS. 4A and 4B can be implemented in various ways. For example, in some embodiments, the system and the component thereof may be implemented as hardware, software, or a combination of software and hardware. The hardware may be implemented using dedicated logics. The software may be stored in a memory and executed by an appropriate instruction execution device, such as a microprocessor, a dedicated design hardware, etc. Those skilled in the art should understand that the above-mentioned methods and systems can be implemented using computer-executable instructions and/or control codes contained in a processor. For example, the control codes may be provided on a carrier medium (e.g., a disk, a CD, or a DVD-ROM), a programmable ROM (PROM), a data carrier such as an optical or electronic signal carrier, etc. In some embodiments, the training system and the component thereof described in the present disclosure may be implemented by semiconductors (e.g., very large scale integrated circuits or gate arrays, logic chips, transistors), hardware circuits of a programmable hardware device (e.g., a field programmable gate array (FPGA), a programmable logic device (PLD)), a software executed by various types of processors, a combination of the hardware circuit and a software (e.g., firmware), etc.

It should be noted that the above description regarding the processing device 120 is merely provided for the purposes of illustration, and not intended to limit the scope of the present disclosure. It will be appreciated that for those skilled in the art, after understanding the principle of the system, the modules may be combined or a sub-system may be constructed to connect to other modules, without departing from the principle of the system. Two or more modules may be combined into a module, and any one of the modules may be divided into two or more units. In some embodiments, the processing device 120*a* and/or the processing device 120*b* may share two or more modules. For example, the processing device 120*a* and the processing device 120*b* may share a common acquisition module, that is, the acquisition module 410 and the acquisition module 450 may be implemented through a single module. In some embodiments, the processing device 120*a* and/or the processing device 120*b* may include one or more additional modules, such as a storage module (not shown) for storing data. In some embodiments, the processing device 120*a* and the processing device 120*b* can be integrated into a single processing device.

Figure 5:
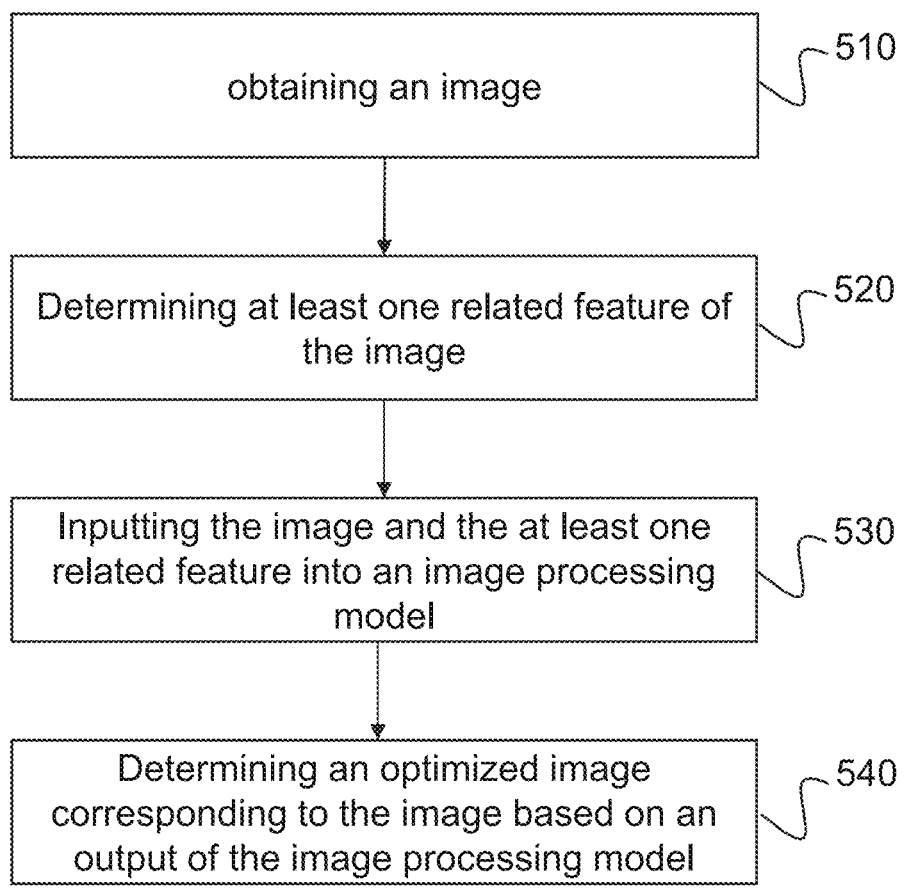
FIG. 5 is a flowchart illustrating an exemplary process for image quality optimization according to some embodiments of the present disclosure.

FIG. 5 is a flowchart illustrating an exemplary process for image quality optimization according to some embodiments of the present disclosure. In some embodiments, process 500 may be executed by the processing device 120*a* or other processing devices. In some embodiments, the process 500 may be implemented as a set of instructions (e.g., an application) stored in a storage device (e.g., the storage device 150, the storage 220, and/or the storage 390). The processing device 120*a* (e.g., the processor 210, the CPU 340, and/or one or more modules illustrated in FIG. 4A) may execute the set of instructions, and when executing the instructions, the processing device 120*a* or the other processing devices may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and the content described below are not intended to be limiting.

In 510, the processing device 120*a* (e.g., the acquisition module 410) may acquire an image to be processed.

The image to be processed may refer to an image (e.g., a 2D image, a 3D image, a 4D image) and/or raw image data (e.g., raw CT data acquired by the imaging device 110). The raw image data may include imaging data. In some embodiments, the image may be an image generated based on the imaging data that is obtained via a scan performed by the imaging device 110 on an imaging subject. For example, the image may be generated by performing an image reconstruction on the imaging data. The reconstruction algorithm may include a filtered-back projection (FBP) algorithm, an algebraic reconstruction technology (ART), a local reconstruction algorithm (LocalRA), an iterative reconstruction algorithm, or the like, or any combination thereof. For convenience, the "image" may be taken as an example hereinafter.

In some embodiments, the imaging device 110 may be imaging devices of different modalities, accordingly, images to be processed may be images of different modalities. For example, the imaging device 110 may be a CT device, accordingly, the image to be processed may be a CT image. As another example, the imaging device 110 may be an MRI device, accordingly, the image to be processed may be an MRI image. The modality of the image is not limited in the embodiments of the present disclosure. For example, the image may also be an X-ray image, a PET image, an SPECT image, or the like, or any combination thereof.

In some embodiments, the image may be an image with relatively low image quality. For example, the image may include, but not limited to, an image containing artifacts, an image containing noise, an image with a low signal-to-noise ratio (SNR), an image with low contrast, an image with low resolution, an image containing motion (e.g., an image in which pixels move), etc.

In some embodiments, the image may be generated and stored in advance in a storage device (e.g., the storage device 150, the storage 220, and/or the storage 390) as described elsewhere in the present disclosure. The processing device 120a (e.g., the acquisition module 410) may acquire the image from the storage device. In some embodiments, the image may be generated by the processing device 120a. For example, the processing device 120a may instruct the imaging device 110 to scan an imaging subject or an imaging target to obtain the imaging data. The processing device 120a may generate the image based on the imaging data. In some embodiments, the acquisition module 410 may obtain the image from the imaging device 110. The imaging device 110 may generate the imaging data via a scan on the imaging subject or the imaging target, and generate the image based on the imaging data. In some embodiments, the acquisition module 410 may call related interfaces to obtain the image from an external device.

In 520, the processing device 120a (e.g., the determination module 420) may determine at least one related feature of the image.

In some embodiments, the at least one related feature may be features directly and/or indirectly related to the image. In some embodiments, the at least one related feature may include an acquisition parameter feature relating to the image, an imaging parameter feature relating to the image, an imaging subject feature of the imaging subject, a quality feature of the image, or the like, or any combination thereof.

In some embodiments, the acquisition parameter feature relating to the image may be a feature related to an acquisition process of the imaging data corresponding to the image, for example, a feature relating to the imaging device 110. Taking the imaging device being a CT device as an example, the acquisition parameter feature may include a voltage parameter, a current parameter, a filtering parameter of a scanning signal, a size of a detector, a response character of the detector to a signal, a sensitive character of the detector to signal motion, an intensity value of a noise generated by the detector, or the like, or any combination thereof.

The voltage parameter may be a value of a voltage applied between a cathode and an anode of an X-ray tube. The voltage parameter may reflect the penetration of X-rays. Generally, under a same condition, the higher the voltage parameter is, the stronger the penetration of X-rays may be, and the worse the contrast of a low-density image may be, and vice versa.

The current parameter may be a value of a current applied on the cathode of the X-ray tube. The current parameter may reflect a radiation dose received by the imaging subject when the imaging subject is scanned. The greater the current parameter is, the more free electrons generated by the cathode may be, the greater the count of free electrons bombarding on an anode target of the X-ray tube may be, the greater the density of the X-ray photons that are ultimately generated may be, and the more the radiation dose received by the imaging subject may be. Since the radiation dose can affect the image quality of the CT image, the current parameter may also reflect the image quality of the image.

The filtering parameter of the scanning signal may be parameter(s) associated with a filter between the X-ray tube and the detector. In some embodiments, the filter between the X-ray tube and the detector may filter out X-rays that are less helpful to the image, thereby reducing the radiation dose of the human body. In some embodiments, the filter between the X-ray tube and the detector may appropriately filter out a portion of X-rays at the edge of the human body based on a shape of the human body, thereby making the X-rays attenuated by the human body more uniform. Therefore, the filtering parameter of the scanning signal may reflect a spatial distribution and/or an intensity distribution of the X-rays received by the imaging subject.

The size of the detector may include a size of the detector itself and/or a size of a receiving unit in the detector.

The response character of the detector to the signal may include a response gain curve and/or a spectral response nonlinear feature. In some embodiments, the response gain curve may reflect a response ratio of the detector to X-rays of different intensities. In some embodiments, the spectral response nonlinear feature may reflect the absorption of X-rays of different energy spectrums and a beam hardening effect.

The sensitive character of the detector to the signal motion may include focus jitter response sensitivity. In some embodiments, the focus jitter response sensitivity may reflect a variation of the X-rays detected by the detector due to the focus jitter of the X-ray tube. For example, due to the jitter of the focus, a slight displacement of the focus position occurs, the X-rays detected by the detector may also change slightly, which may affect the quality of the imaging data, thereby affecting the image quality.

The intensity value of the noise generated by the detector may be an intensity of image noise caused by an electrostatic flow generated in the detector. In some embodiments, the intensity value of the noise generated by the detector may include an electronic noise of the detector which may be an electronic noise generated by the inherent physical limitation of the system, for example, an electronic noise in a photomultiplier tube of the detector, an electronic noise in a data acquisition system, etc.

In some embodiments, the acquisition parameter feature may also include a type of an imaging device, a type of the detector, a type of the X-ray tube (e.g., a type of a target surface of an anode target included in the X-ray tube), a mechanical parameter (e.g., a distance from a radiation source to the center of rotation, a distance from the radiation source to the detector) of the imaging device, or the like, or any combination thereof.

In some embodiments, the imaging parameter feature relating to the image may include a parameter associated with an image reconstruction process. Taking a CT image as an example, the imaging parameter feature may include a count of pixels, a pixel pitch, a reconstruction thickness, a reconstruction interval, a convolution kernel parameter, or the like, or any combination thereof.

A count of pixels refers to a count (e.g., 512*512, 1024*1024) of all pixels included in an image. A pixel pitch refers to a distance between two adjacent pixel points in an image.

A reconstruction thickness refers to a thickness of a CT scanning layer, that is, a thickness of one layer of an image. In some embodiments, different reconstruction thicknesses may be set according to a scanning portion, a lesion position, a need of a diagnostic doctor, etc. In some embodiments, the reconstruction thickness may be 10 mm, 7 mm, 5 mm, 1 mm, etc. A reconstruction interval refers to a distance between CT scanning layers, that is, a distance between two layers of images.

The convolution kernel parameter may include a count of convolution kernels, a size of the convolution kernel, etc.

In some embodiments, the imaging subject feature may include a stature (e.g., height, weight, body type) of the imaging subject, an age of the imaging subject, a gender of the imaging subject, a body density of the imaging subject, an attenuation distribution of the imaging subject to X-rays, a density of an imaging target (e.g., an organ, a tissue) of the imaging subject, an attenuation distribution of the imaging target to X-rays, a density of each of a plurality of scanning layers of the imaging subject, an attenuation distribution of each of the plurality of scanning layers of the imaging subject to X-rays, a density of each of a plurality of scanning layers of the imaging target, or an attenuation density of each of the plurality of scanning layers of the imaging target to X-rays, or the like or any combination thereof.

The imaging subject feature may directly or indirectly affect the attenuation of X-rays, which may affect the image quality. For example, the attenuation of X-rays corresponding to a relatively fat imaging subject may be relatively large, accordingly, the noise of the image may be relatively large. The attenuation of X-rays corresponding to a relatively thin imaging subject may be relatively small, accordingly, the noise of the image may be relatively small. As another example, different imaging targets (e.g., different organs) may have different effects on the attenuation of X-rays, and accordingly, may have different effects on the image quality.

In some embodiments, the determination module 420 may determine the imaging subject feature based on historical data. For example, the determination module 420 may determine a density of the imaging target (e.g., an organ, a tissue) of the imaging subject based on a historical image (e.g., a CT image, an X-ray image, an MRI image, a PET-CT image) of the imaging subject. In some embodiments, the determination module 420 may determine the imaging subject feature based on data acquired in real-time. For example, the determination module 420 may determine the stature of the imaging subject, the body density of the imaging subject, etc., based on an image acquired in real-time by a camera or data acquired by other sensors (e.g., a weight scale set on the table 114). In some embodiments, the determination module 420 may determine the imaging subject feature based on information input by a user (e.g., a doctor). For example, the user may input the age of the imaging subject, the gender of the imaging subject, etc., via the terminal device 130.

The X-ray attenuation distribution represents an attenuation of X-ray distribution values. In some embodiments, the determination module 420 may acquire the attenuation distribution of each of a plurality of scanning layers of the imaging subject or the imaging target to X-rays based on a scout image (e.g., a CT scout image). In some embodiments, the determination module 420 may determine the attenuation distribution of the imaging subject, the imaging target, or each of the plurality of scanning layers of the imaging subject or the imaging target to X-rays based on an equivalent diameter of a phantom. For example, the equivalent diameter of the phantom may be determined based on a scout image. The equivalent diameter of the phantom may be converted into an attenuation distribution of X-rays through a standard conversion technique.

In some embodiments, the quality feature may include a noise feature, an artifact feature, a motion feature, a grayscale feature, a resolution, a contrast of the image, or the like, or any combination thereof.

In some embodiments, the noise feature may include a noise distribution, a noise intensity, a noise rate, or the like, or any combination thereof.

The noise intensity may refer to a value of a noise pixel that reflects a noise amplitude in the noise pixel. A global noise intensity may reflect an average noise intensity or a weighted average noise intensity in the image. The noise distribution may reflect a distribution of different noise intensities or different noise amplitudes in the image (e.g., a probability density of different noise intensities).

In some embodiments, the noise distribution may be represented by a noise distribution map, a noise distribution function, etc. In some embodiments, the determination module 420 may generate the noise distribution of the image based on an image reconstruction operation. More descriptions regarding the generating of the noise distribution based on the image reconstruction operation may be found elsewhere in the present disclosure (e.g., FIG. 6A and the descriptions thereof).

In some embodiments, the determination module 420 may determine the noise distribution by a noise extraction algorithm. In some embodiments, the noise extraction algorithm may include a noise statistical model (e.g., a Gaussian noise model, a pulse noise model, a Rayleigh noise model, an index distribution noise model, a uniform distribution noise model, and other random noise models) and/or a probability density function (PDF) corresponding to the noise statistical model.

The noise rate may reflect a dispersion degree of the noise distribution. In some embodiments, the determination module 420 may determine the noise rate based on a variance and/or a standard deviation of the noise distribution.

In some embodiments, the processing device 120a may determine the noise feature of the image using an image block technique, a filter technique, a null domain sampling technique, a Bayesian estimate technique, or the like, or any combination thereof.

In some embodiments, an artifact of an image may refer to a portion of the image that does not correspond to any portion of the imaging subject that actually exists, which may cause image distortion, image overlap, or image missing. In some embodiments, the artifact feature may include an artifact distribution, an artifact intensity, a global artifact intensity, an artifact ratio, or the like, or any combination thereof.

An artifact intensity may refer to a value of an artifact pixel, which reflects an artifact amplitude of the artifact pixel. A global artifact intensity may reflect an average artifact intensity or a weighted average artifact intensity of an image. An artifact distribution may reflect a distribution of different artifact intensities in an image (e.g., a probability density of different artifact intensities). In some embodiments, the artifact distribution may be represented by an artifact distribution map or an artifact distribution function, etc. An artifact ratio may reflect a dispersion degree of the artifact distribution.

In some embodiments, the determination module 420 may identify artifact(s) in the image and determine the artifact feature. In some embodiments, the processing device 120a may determine the artifact feature using a feature extraction algorithm. The feature extraction algorithm may include a histogram of gradient (HOG), a local binary pattern (LBP) algorithm, a scale invariant feature transform (SIFT) algorithm, a Haar-like features algorithm, a gray-level co-occurrence matrix (GLCM) algorithm, a Hough transform algorithm, a Fourier transform algorithm, a Fourier shape descriptor method, a shape parameter method, a finite element method (FEM), a rotation function, a wavelet descriptor, or the like, or any combination thereof. Similar to the noise feature, the processing device 120a may also determine the artifact feature based on a statistical model and/or a probability density function (PDF) corresponding to the statistical model.

In some embodiments, the motion feature may reflect a movement status of pixel points in the image. The motion feature may include a motion intensity, a motion direction, a motion position, or the like, or any combination thereof. In some embodiments, the determination module 420 may determine a motion vector distribution based on a motion vector extraction algorithm. In some embodiments, the motion vector extraction algorithm may include a motion vector field adaptive search technique (MVFAST), an image block matching motion estimation algorithm, a pixel technique, and a feature technique, or the like, or any combination thereof.

In some embodiments, the grayscale feature may include a grayscale distribution and/or a global grayscale distribution. In some embodiments, the grayscale distribution may reflect a distribution of grayscale values of pixels in the image. The global grayscale distribution may reflect an overall distribution (e.g., an average grayscale value of the pixels and/or a weighted average grayscale value of the pixels) of grayscale values of the pixels in the image. In some embodiments, the determination module 420 may determine the grayscale feature using a histogram of gradient (HOG) and/or a localized binary pattern (LBP) algorithm.

In some embodiments, a resolution may be a count of pixel points contained in an image per inch. Generally, the higher the resolution of the image is, the clearer the image may be.

In some embodiments, a contrast may reflect a measurement of different brightness levels between a brightest white area and a darkest black area of an image, which may reflect a magnitude of a grayscale contrast of the image. Generally, the larger the contrast is, the clearer the image may be and the more vivid the color may be.

In some embodiments, the determination module 420 may determine the quality feature based on a machine learning model. Specifically, the determination module 420 may input at least one of the acquisition parameter feature, the imaging parameter feature, or the imaging subject feature into a feature processing model. The determination module 420 may determine the quality feature of the image based on an output of the feature processing model. More descriptions regarding the determination of the quality feature based on the machine learning model may be found elsewhere in the present disclosure (e.g., FIG. 6B and the descriptions thereof).

In some embodiments, the determination module 420 may determine different quality features according to an image quality optimization purpose (or an application scenario of image quality optimization). For example, if the image quality optimization purpose is denoising, the quality feature may be a noise feature. If the image quality optimization purpose is decreasing artifact, the quality feature may be an artifact feature. If the image quality optimization purpose is motion correction, the quality feature may be a motion feature. If the image quality optimization purpose is increasing resolution, the quality feature may be a resolution. If the image quality optimization purpose is increasing image contrast, the quality feature may be a contrast of an image. If the image quality optimization purpose is correcting scattering, the quality feature may be an artifact feature. The essence of the scattering correction is to correct a discrepancy between actual acquisition data and estimated data caused by the scattering of X-rays which refers to a phenomenon that X-rays reflect on the surface of the detector or its internal structures to produce extra rays. Due to the existence of scattering, artifacts may be generated in a reconstructed image. It will be appreciated that the above examples only represent the minimum quality features required to achieve the image quality optimization purpose, and multiple quality features may be selected according to actual requirements to enhance the representation of image quality. For example, if the image quality optimization purpose is the contrast, the quality feature may include the contrast, the resolution, and the contrast.

In 530, the processing device 120a (e.g., the inputting module 430) may input the image and the at least one related feature into an image processing model.

In some embodiments, the image processing model may be a pre-trained machine learning model for optimizing an image based on the image and/or at least one related feature to achieve an optimization purpose corresponding to the image. In some embodiments, the image processing model may be a deep learning model. The deep learning model may include a deep neural network (DNN) model, a multilayer neural network (MLP) model, a convolutional neural network (CNN) model, a generative adversarial network (GAN) model, and/or a deep convolution coding decoding (DCED) neural network model. More descriptions regarding the training process for the image processing model may be found elsewhere in the present disclosure (e.g., FIG. 7 and the descriptions thereof).

In some embodiments, the processing device 120a may select the image processing model based on at least one of the acquisition parameter feature, the imaging parameter feature, or the imaging subject feature. For example, the processing device 120 may train an image processing model corresponding to acquisition parameter feature by inputting sample images and acquisition parameter features. Accordingly, when performing an optimization based on an image and its acquisition parameter feature, the processing device 120 may acquire an image processing model corresponding to the acquisition parameter feature. As another example, the processing device 120 may train an image processing model corresponding to acquisition parameter feature and imaging subject feature by inputting sample images, sample acquisition parameter features, and sample subject features. Accordingly, when performing an optimization based on an image and its acquisition parameter feature and imaging subject feature, the processing device 120 may acquire an image processing model corresponding to the acquisition parameter feature and the imaging subject feature. It should be understood that the processing device 120 may also perform other combinations based on the relevant features, and obtain the corresponding image processing model.

The acquisition parameter feature and/or the imaging parameter feature may reflect the type of the imaging device (i.e., a modality of the imaging device, for example, a CT device, an MRI device, or a PET device) that acquires the image. The imaging subject feature may reflect the subject type or imaging target type in the image. In the present disclosure, a subject and/or an imaging target may be simply referred to as "subject," a subject type and/or an imaging target type may be simply referred to as "subject type."

In some embodiments, the processing device 120*a* may select the image processing model corresponding to the subject type based on the subject type. In some embodiments, the image processing model (e.g., an image processing model corresponding to "chest") may be trained based on a plurality of training samples (e.g., sample chest images) associated with the subject type. More descriptions regarding the training of the image processing model corresponding to the subject type may be found elsewhere in the present disclosure (e.g., FIG. 11 and relevant description thereof). In some embodiments, the processing device 120 may select the image processing model corresponding to the imaging device type based on the imaging device type. In some embodiments, the image processing model (e.g., an image processing model corresponding to the CT device) corresponding to the imaging device type may be trained based on a plurality of training samples (e.g., sample CT images) related to the imaging device type. More descriptions regarding the training of the image processing model corresponding to the imaging device type may be found elsewhere in the present disclosure (e.g., FIG. 10 and relevant description thereof).

In some embodiments, the imaging parameter feature may also reflect a reconstruction algorithm of the image. In some embodiments, the processing device 120 may select the image processing model corresponding to the reconstruction algorithm based on the reconstruction algorithm. In some embodiments, the image processing model corresponding to the reconstruction algorithm (e.g., an image processing model corresponding to an iterative reconstruction algorithm) may be trained based on a plurality of training samples (e.g., sample iteration reconstruction images) associated with the reconstruction algorithm.

In some embodiments, different reconstruction algorithms may introduce different noise types and/or artifact types. The processing device 120 may select the image processing model based on a noise type, an artifact type, or a motion type. Similarly, the image processing model (e.g., an image processing model corresponding to a Gaussian noise) corresponding to the noise type may be trained based on a plurality of training samples (e.g., sample Gaussian noise images) related to the noise type. In some embodiments, the image processing model (e.g., an image processing model corresponding to a strip artifact) corresponding to the artifact type may be trained based on a plurality of training samples (e.g., sample strip artifact images) associated with the artifact type. Similarly, the processing device 120 may train an image processing model corresponding to a motion type.

In some embodiments, the processing device 120*a* may obtain the image processing model from a storage device (e.g., the storage device 150) of the image quality optimization system 100 or from an external resource via a network (e.g., the network 140). For example, the image processing model may be trained and stored in advance in the storage device of the image quality optimization system 100. The processing device 120 may access the storage device and acquire the image processing model. In some embodiments, the image processing model may be generated by a training device (e.g., the processing device 120) according to a training process (e.g., processes 700, 1000, 1100).

In some embodiments, the inputting module 430 may process at least one related feature and input the processed feature into the image processing model. For example, the inputting module 430 may convert the at least one related feature to a vector or a matrix, then fuse (e.g., add, multiply, splice) the vector or matrix, and input the fused vector or matrix into the image processing model.

In some embodiments, before inputting the image and the at least one related feature into the image processing model, the processing device 120 may preprocess the image. The preprocessing may include image reconstruction, image normalization, etc. Merely by way of example, the processing device 120 may perform an image resampling operation on the image to determine a resampled image having a preset size. Then, the processing device 120 may normalize the resampled image such that pixel (or voxel) values of the normalized image can be within a preset range (e.g., [−1, 1]). Further, the processing device 120 may input the normalized image and the at least one related feature into the image processing model.

In 540, the processing device 120*a* (e.g., the optimization module 440) may determine an optimized image corresponding to the image based on an output of the image processing model.

In some embodiments, as described above, the determination module 420 may determine different quality features based on the image quality optimization purpose. Accordingly, the optimization module 440 may determine different optimized images. For example, if the image quality optimization purpose is denoising or increasing resolution, the optimized image may be an image (e.g., a denoised image) with a noise level lower than that of the image or an image with a resolution higher than that of the image. As another example, if the image quality optimization purpose is decreasing artifact, the optimized image may be an image (e.g., an image with artifacts decreased/removed) with an artifact level lower than that of the image.

In some embodiments, the optimization module 440 may determine the output of the image processing model as the optimized image. In some embodiments, after determining the optimized image, the optimization module 440 may further process the optimized image, for example, smooth the optimized image, adjust the resolution or contrast, adjust brightness, etc. In some embodiments, the optimization module 440 may also transmit the optimized image or the processed optimized image to the terminal device 130 for display. In some embodiments, the optimization module 440 may also transmit the optimized image or the processed optimized image to the storage device 150 for storage.

According to some embodiments of the present disclosure, by introducing the related features (e.g., the acquisition parameter feature, the imaging parameter feature, the imaging subject feature, the quality feature) of multiple dimensions of the image, the image processing model can better understand the information of the image, so as to better achieve the optimization purpose.

Figure 6A:
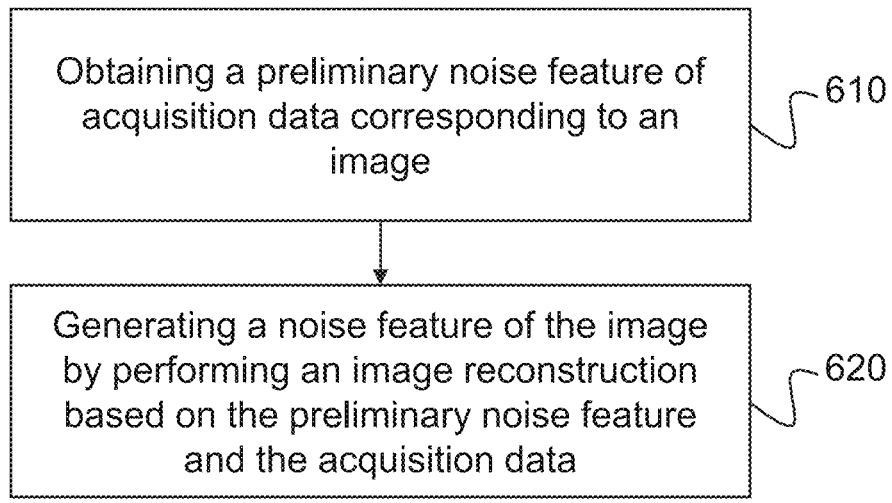
FIG. 6A is a flowchart illustrating an exemplary process for generating a noise feature of an image based on an image reconstruction process according to some embodiments of the present disclosure.

FIG. 6A is a flowchart illustrating an exemplary process for generating a noise feature of an image based on an image reconstruction process according to some embodiments of the present disclosure. In some embodiments, process 600a may be executed by the processing device 120a or other processing devices. In some embodiments, the process 600a may be implemented as a set of instructions (e.g., an application) stored in a storage device (e.g., the storage device 150, the storage 220, and/or the storage 390). The processing device 120a (e.g., the processor 210, the CPU 340, and/or one or more modules illustrated in FIG. 4A) may execute the set of instructions, and when executing the instructions, the processing device 120a may be configured to perform the process 600a. The operations of the illustrated process presented below are intended to be illustrative. In some embodiments, the process 600a may be accomplished with one or more additional operations not described and/or without one or more of the operations discussed. Additionally, the order of the operations of the process 600a illustrated in FIG. 6A and the content described below are not intended to be limiting.

In 610, the processing device 120a (e.g., the determination module 420) may obtain a preliminary noise feature of acquisition data corresponding to an image.

In some embodiments, the acquisition data corresponding to the image may refer to scanning data (also referred to as "raw data" or "imaging data") acquired during a scanning process. Taking a CT image as an example, scanning data corresponding to the CT image may refer to X-ray data detected by the detector 112.

In some embodiments, the determination module 420 may obtain the preliminary noise feature in various ways. In some embodiments, the determination module 420 may determine the preliminary noise feature (e.g., a preliminary noise distribution) based on acquisition signals of the acquisition data. Specifically, the determination module 420 may obtain at least one acquisition signal intensity corresponding to the acquisition data. The determination module 420 may determine at least one noise amplitude corresponding to the at least one acquisition signal intensity. The determination module 420 may determine the preliminary noise feature of the acquisition data based on the at least one noise amplitude.

In some embodiments, the acquisition signal intensity may be an intensity of an electrical signal collected by the detector 112. Specifically, the detector 112 may collect X-rays passing through the imaging subject, and convert collected photons into an electrical signal. Accordingly, the intensity of the electrical signal may characterize a count of photons collected by the detector 112.

In some embodiments, the determination module 420 may determine at least one noise amplitude corresponding to the at least one acquisition signal intensity based on a statistical law. In some embodiments, the statistical law may be a statistical law formed based on interaction between X-rays and the detector 112. In some embodiments, the statistical law may include a relationship between the count of photons collected by the detector 112 and a noise. For example, the count of photons collected by the detector 112 may be proportional to an expectation (e.g., a noise amplitude or a variance of the noise amplitude) of noise. As mentioned above, the intensity of the acquisition signal may characterize the count of photons collected by the detector 112. Therefore, the determination module 420 may determine at least one noise amplitude corresponding to the at least one of acquisition signal intensity based on the statistical law.

In 620, the processing device 120a (e.g., the determination module 420) may generate the noise feature of the image by performing an image reconstruction process based on the preliminary noise feature and the acquisition data.

In some embodiments, the determination module 420 may perform the image reconstruction process using a reconstruction algorithm. The reconstruction algorithm may include a Fourier slice-theorem algorithm, a filtered back-projection algorithm (FBP), a fan beam reconstruction algorithm, an iterative reconstruction algorithm, an analytical reconstruction algorithm, an algorithm based on compressed sensing (CS), or the like, or any combination thereof. In some embodiments, since the image reconstruction process requires a reconstruction parameter (i.e., an imaging parameter feature), the determination module 420 may generate the noise feature (e.g., a noise distribution) of the image by performing the image reconstruction process based on the preliminary noise feature (e.g., the preliminary noise distribution), the acquisition data, and the imaging parameter feature.

In some embodiments, when any one of the noise features is determined, the determination module 420 may determine other features of the noise features. For example, when the determination module 420 determines the noise distribution, the determination module 420 may determine a noise intensity or a noise rate via a preset conversion relationship.

Figure 6B:
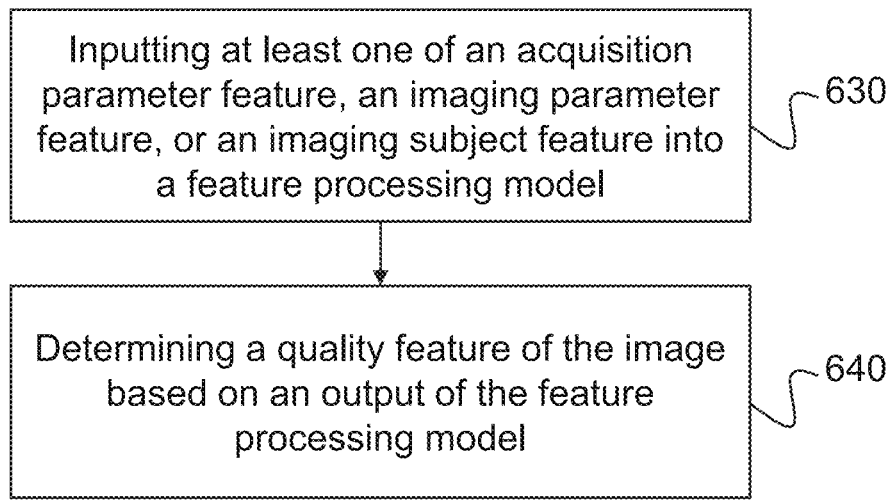
FIG. 6B is a flowchart illustrating an exemplary process for determining a quality feature of an image based on a feature processing model according to some embodiments of the present disclosure.

FIG. 6B is a flowchart illustrating an exemplary process for determining a quality feature of an image based on a feature processing model according to some embodiments of the present disclosure. In some embodiments, process 600b may be executed by the processing device 120a or other processing devices. In some embodiments, the process 600b may be implemented as a set of instructions (e.g., an application) stored in a storage device (e.g., the storage device 150, the storage 220, and/or the storage 390). The processing device 120a (e.g., the processor 210, the CPU 340, and/or one or more modules illustrated in FIG. 4A) may execute the set of instructions, and when executing the instructions, the processing device 120a may be configured to perform the process 600b. The operations of the illustrated process presented below are intended to be illustrative. In some embodiments, the process 600b may be accomplished with one or more additional operations not described and/or without one or more of the operations discussed. Additionally, the order of the operations of the process 600b illustrated in FIG. 6B and the content described below are not intended to be limiting.

In 630, the processing device 120a (e.g., the determination module 420) may input at least one of an acquisition parameter feature, an imaging parameter feature, or an imaging subject feature into a feature processing model.

In some embodiments, the feature processing model may be a pre-trained machine learning model. In some embodiments, the feature processing model may include a convolutional neural network (CNN) model, a support vector machine (SVM), a Naive Bayes, a decision tree, etc. In some embodiments, the feature processing model may be determined by training a preliminary feature processing model based on a plurality of sample images and a plurality of reference quality features (the reference quality features may be regarded as labels of the sample images) corresponding to the plurality of sample images. In some embodiments, the sample image may be a medical image of any modality of an imaging subject, such as a CT image, an X-ray image, an MR image, a PET-CT image, etc. In some embodiments, the sample image may also be a body image of the imaging subject. For example, the sample image may be a front image, a side image, etc., of a patient taken by a camera. In some embodiments, taking a single sample image as an example, the corresponding reference quality feature (i.e., the label) may be represented by a quality feature graph (e.g., a reference noise distribution map, a reference artifact distribution map, a reference motion vector distribution map), a quality feature matrix, etc.

In some embodiments, the plurality of sample images and the plurality of reference quality features corresponding to the plurality of sample images may be inputted into the preliminary feature processing model. The preliminary feature processing model may process the plurality of sample images and determine the corresponding sample quality features. Further, one or more model parameters may be iteratively updated based on a difference between the sample quality features and the corresponding reference quality features until the training is completed. For example, a value of a loss function may be determined based on a difference between the sample quality features and the reference quality features. Further, the model parameters may be adjusted to make the value of the loss function as small as possible until the training is completed.

In 640, the processing device 120a (e.g., the determination module 420) may determine a quality feature of the image based on an output of the feature processing model.

In some embodiments, similar to the reference quality feature, the quality feature of the image outputted by the model may be represented by a quality feature graph (e.g., a noise distribution map, an artifact distribution map, a motion vector distribution map), a quality feature matrix, etc.

FIG. 7 is a flowchart illustrating an exemplary process for training an image processing model according to some embodiments of the present disclosure. In some embodiments, process 700 may be executed online or offline by the processing device 120b or other processing devices. For example, the process 700 may be implemented as a set of instructions (e.g., an application) stored in a storage device (e.g., the storage device 150, the storage 220, and/or the storage 390). The processing device 120b (e.g., the processor 210, the CPU 340, and/or one or more modules illustrated in FIG. 4B) may execute the set of instructions, and when executing the instructions, the processing device 120b may be configured to perform the process 700. The operations of the illustrated process presented below are intended to be illustrative. In some embodiments, the image processing model described in operation 530 in FIG. 5 may be obtained according to the process 700.

In 710, the processing device 120b (e.g., the acquisition module 450) may obtain a plurality of training samples and a plurality of standard images corresponding to the plurality of training samples.

In some embodiments, each of the plurality of training samples may include a sample image and at least one sample related feature of the sample image. In some embodiments, the sample image may be related to a training target of the image processing model, that is, the sample image may be related to an application scenario of the image processing model. For example, if the application scenario of the image processing model is denoising, the sample image may be an image with noises added. As another example, if the application scenario of the image processing model is decreasing artifacts, the sample image may be an image with artifacts added. As still an example, if the application scenario of the image processing model is increasing resolution, the sample image may be an image with resolution reduced. In some embodiments, the plurality of training samples may correspond to a plurality of quality levels (e.g., a plurality of noise intensities, a plurality of artifact intensities).

In some embodiments, the plurality of training samples may be generated and stored in advance in a storage device (e.g., the storage device 150 or an external database) disclosed elsewhere in the present disclosure. The processing device 120 may acquire the plurality of training samples directly from the storage device.

In some embodiments, the plurality of sample images and/or the plurality of standard images may be determined based on historical data. For example, a historical image (e.g., a historical CT image) corresponding to an imaging subject may be used as a sample image. The sample image may be processed (e.g., processed to reduce noise, processed to decrease artifacts, processed to increase resolution) to generate a standard image. A way of processing the sample image may be associated with a training target of the image processing model.

In some embodiments, at least a portion of the plurality of training samples may be generated by the processing device 120. Merely by way of example, the processing device 120 may preprocess at least one qualified image to determine the plurality of sample images and the plurality of standard images. The qualified image may refer to an image whose quality feature satisfies a quality requirement. More details regarding the plurality of sample images and the plurality of standard images may be found elsewhere in the present disclosure (e.g., FIG. 8 and the descriptions thereof).

In some embodiments, the at least one sample related feature may include a sample acquisition parameter feature relating to the sample image, a sample imaging parameter feature relating to the sample image, a sample imaging subject feature of a sample imaging subject, a sample quality feature of the sample image, or the like, or any combination thereof. In some embodiments, the sample quality feature may include a sample noise feature, a sample artifact feature, a sample motion feature, a sample grayscale feature, a sample resolution, a sample contrast, or the like, or any combination thereof of the sample image. More descriptions regarding the at least one sample related feature may be found in the descriptions of the at least one related feature of the image in operation 520.

In some embodiments, each of the plurality of training samples may further include a weight of each of the at least one sample related feature. By assigning different weights to different sample related features, the preliminary image processing model may learn different training samples using different channels, so that the trained image processing model can have better predictive capabilities to unlearned training samples.

In 720, the processing device 120b (e.g., the training module 460) may determine the image processing model by training the preliminary image processing model based on the plurality of training samples and the plurality of standard images.

In some embodiments, before inputting the plurality of training samples and the plurality of standard images into the preliminary image processing model, the plurality of training samples and the plurality of standard images may be processed, and the plurality of processed training samples and the plurality of processed standard images may be inputted into the preliminary image processing model. For example, the plurality of sample images, the sample related features of the plurality of sample images, and the plurality of standard images may be converted into a first matrix, a second matrix, and a third matrix. The first matrix, the second matrix, and/or the third matrix may be fused. The fused matrix may be inputted into the preliminary image processing model. In some embodiments, the fusion may include, but not limited to, matrix addition, matrix multiplication, matrix splicing, etc. In some embodiments, the fusion may also be performed after the plurality of training samples and the plurality of standard images are inputted into the preliminary image processing model. For example, the fusion may be performed at an input layer of the preliminary image processing model.

In some embodiments, in the at least one sample related feature, except for the sample quality feature, the other features (e.g., the sample acquisition parameter feature, the sample imaging parameter feature, the sample imaging subject feature) are usually discrete values and can't be directly used as an input of the input layer of the preliminary image processing model. Accordingly, in some embodiments, the discrete values may be converted to a fourth matrix, and the fourth matrix may be input as an input of an intermediate layer of the preliminary image processing model.

In some embodiments, the plurality of training samples and the plurality of standard images (used as the labels of the training samples) may be inputted into the preliminary image processing model. In some embodiments, the preliminary image processing model may include a deep learning model, such as a DNN model, an MLP model, a CNN model, a GAN model, a DCED network model. In some embodiments, the preliminary image processing model may include at least one preliminary model parameter. The at least one preliminary model parameter may be a default setting of the image quality optimization system 100 or may be adjusted based on different situations. Taking the CNN model as an example, the at least one preliminary model parameter may include a count of convolution layers, a count of convolution kernels, a volume of the convocation kernel, a step size, a parameter of each convolution layer, or the like, or any combination thereof.

The preliminary image processing model may process the plurality of training samples and determine their corresponding sample optimized images. Further, the model parameter may be iteratively updated based on the plurality of sample optimized images and the plurality of standard images until the training is completed. For example, a value of a loss function may be determined based on a difference between the plurality of sample optimized images and the plurality of standard images. Further, the model parameters may be adjusted to make the value of the loss function as small as possible until the training is completed.

In some embodiments, the loss function of the image processing model may be positively correlated with a quality weight. The quality weight may be determined based on the sample quality feature. In some embodiments, the quality weight may be associated with a quality level of the sample image. For example, the loss function in a current iteration may be determined according to the following Equation (1):

$$L = \Sigma_1^n w_i * l(f(x_i), y_i), \quad (1)$$

where L denotes the loss function, n denotes a count of the plurality of training samples, $x_i$ denotes a sample image in an i-th training sample (also referred to as "i-th sample image"), $f(x_i)$ denotes an i-th predicted optimized image corresponding to the i-th sample image, $y_i$ denotes an i-th qualified image (used as the standard image) corresponding to the i-th sample image, $l(f(x_i),y_i)$ denotes a loss (e.g., a square loss, an absolute value loss) related to a difference between the i-th predicted optimized image and the i-th qualified image, and $w_i$ denotes an i-th quality weight corresponding to the i-th training sample.

In some embodiments, the loss function may be further normalized according to the following Equation (2):

$$L = \sum_1^n \frac{w_i * l(f(x_i), y_i)}{m_i^c}, \quad (2)$$

where $m_i$ denotes an i-th sample quality feature of the i-th sample image and c denotes a constant for controlling a standardization degree of the sample quality feature. In some embodiments, different training samples may correspond to different quality weights. Taking a specific training sample as an example, a quality weight may be determined based on one or more sample quality features of the specific sample image in the training sample. For example, for each of the one or more sample quality features, the processing device 120b may determine a quality sub-weight corresponding to the sample quality feature. Further, the processing device 120b may determine the quality weight based on one or more quality sub-weights corresponding to the one or more sample quality features. For example, the processing device 120 may determine a comprehensive result (e.g., a weighted sum value, a product value, an average value) of the one or more quality sub-weights as the quality weight.

In some embodiments, according to different image quality optimization purposes, the quality weight and/or the quality sub-weights may be negatively or positively correlated with the sample quality feature, thereby balancing the effects of different training samples on the training of the model. For example, for a model for "reducing noise," the plurality of training samples may include sample images with a relatively high sample noise intensity and sample images with a relatively low sample noise intensity. During the training process, a value of the loss function may be easily decreased by optimizing the sample images with the relatively high sample noise intensity. Thus, to balance the effects of the sample images with the relatively high or low sample noise intensity on the loss function, a quality weight corresponding to a sample image with the relatively high sample noise intensity may be less than a quality weight corresponding to a sample image with the relatively low sample noise intensity. Other noise features (e.g., a noise rate) may be similar to the noise intensity, which may not be repeated here. In some embodiments, the quality weight may be negatively correlated with the sample noise feature.

As another example, the plurality of training samples may include sample images (e.g., a sample CT image including a subject (e.g., a bone, a lung) with a relatively high structural difference) with a relatively high sample contrast and sample images (e.g., a sample CT image including a subject (e.g., a soft tissue such as liver) with a relatively low structural difference) with a relatively low sample contrast. During the training process, a value of the loss function may be easily decreased by optimizing the sample images with the relatively high sample contrast. Thus, to balance the effects of the sample images with the relatively high or low sample contrast on the loss function, a quality weight corresponding to a sample image with the relatively high sample contrast may be less than a quality weight corresponding to a sample image with the relatively low sample contrast. In some embodiments, the quality weight may be negatively correlated with the sample contrast.

As further another example, similarly, for a model for "reducing artifact," a quality weight corresponding to a sample image with a relatively high sample artifact intensity may be less than a quality weight corresponding to a sample image with a relatively low sample artifact intensity. In some embodiments, the quality weight may be negatively correlated with the sample artifact feature.

As still an example, similarly, for a model for "reducing motion," a quality weight corresponding to a sample image with a relatively high sample motion intensity may be less than a quality weight corresponding to a sample image with a relatively low sample motion intensity. Other motion features (e.g., a motion position) may be similar to the motion intensity, which may not be repeated here. In some embodiments, the quality weight may be negatively correlated with the sample motion feature.

As still another example, for a model for "increasing resolution," the plurality of training samples may include sample images with a relatively high sample resolution and sample images with a relatively low sample resolution. During the training process, a value of the loss function may be easily decreased by optimizing the sample images with the relatively low sample resolution. Thus, to balance the effects of the sample images with the relatively high or low sample contrast on the loss function, a quality weight corresponding to a sample image with the relatively high sample resolution may be greater than a quality weight corresponding to a sample image with the relatively low sample resolution. In some embodiments, the quality weight may be positively correlated with the sample resolution.

In some embodiments, the quality weight may be expressed as Equation (3) as below:

$$w_i = A_i^x + B_i^y, \quad (3)$$

where $w_i$ denotes an i-th quality weight of the i-th training sample, $A_i$ denotes a first sample quality feature of the i-th training sample, $B_i$ denotes a second sample quality feature of the i-th training sample, $A_i^x$ denotes a first quality sub-weight of the first sample quality feature, $B_i^y$ denotes a second quality sub-weight of the second sample quality feature, and x and y may be greater or less than 0. When a value of x (or y) is greater than 0, the quality weight may be positively correlated with the first sample quality feature (or the second sample quality feature). When a value of x (or y) is less than 0, the quality weight may be negatively correlated with the first sample quality feature (or the second sample quality feature). The values of x and y may be default settings of the image quality optimization system 100, or may be set by an operator of the image quality optimization system 100, so as to balance the effects of the first sample quality feature and the second sample quality feature on the training of the model.

In some embodiments, the processing device 120b may determine image processing models corresponding to different subject types and/or different scanning device types. More descriptions may be found elsewhere in the present disclosure (e.g., FIGS. 10-11 and the descriptions thereof). In some embodiments, the processing device 120b may determine image processing models corresponding to different related features (i.e., the acquisition parameter feature, the imaging parameter feature, and/or the imaging subject feature). In some embodiments, the processing device 120b may determine image processing models corresponding to different noise types, different artifact types, and/or different motion types.

According to some embodiments of the present disclosure, during the training process of the image processing model, a sample image and at least one sample related feature of the sample image may be used as a training sample to train the preliminary image processing model. The at least one sample related feature can involve multiple dimensions (e.g., the acquisition parameter feature, the imaging parameter feature, the imaging subject feature, the quality feature), which can prompt the preliminary image processing model to better learn information of the multiple dimensions of the sample image, so as to better achieve the optimization purpose.

FIG. 8 is a flowchart illustrating an exemplary process for obtaining a plurality of training samples according to some embodiments of the present disclosure. In some embodiments, process 800 may be executed online or offline by a processing device (e.g., the processing device 120b or other processing devices). For example, the process 800 may be implemented as a set of instructions (e.g., an application) stored in a storage device (e.g., the storage device 150, the storage 220, and/or the storage 390). The processing device 120b (e.g., the processor 210, the CPU 340, and/or one or more modules illustrated in FIG. 4B) may execute the set of instructions, and when executing the instructions, the processing device 120b may be configured to perform the process 800. The operations of the illustrated process presented below are intended to be illustrative. In some embodiments, one or more operations of the process 800 may be performed to achieve at least part of operation 530 as described in connection with FIG. 5.

In 810, the processing device 120b (e.g., the acquisition module 450) may acquire at least one qualified image.

In some embodiments, the qualified image may be an image whose image quality satisfies a preset requirement. In some embodiments, the qualified image may be related to a training target of an image processing model, that is, the qualified image may be related to an application scenario associated with the image processing model. For example, if the application scenario of the image processing model is denoising, the qualified image may be an image whose noise satisfies a preset requirement (e.g., a noise level is below a preset threshold). As another example, if the application scenario of the image processing model is decreasing artifacts, the qualified image may be an image whose artifact satisfies a preset requirement (e.g., an artifact level is below a preset threshold). As a further example, if the application scenario of the image processing model is increasing resolution, the qualified image may be an image whose resolution satisfies a preset requirement (e.g., a resolution is above a preset threshold). As still a further example, if the application scenario of the image processing model is motion correction, the qualified image may be an image whose motion satisfies a preset requirement (e.g., a motion level is below a preset threshold). In some embodiments, the preset requirement may be a system default value or may be adjusted according to actual requirements.

In 820, the processing device 120b (e.g., the acquisition module 450) may generate a plurality of training samples by preprocessing the at least one qualified image.

In some embodiments, the preprocessing may include segmentation, adding noise, adding artifacts, reducing resolution, adding motion, or the like, or any combination thereof. As mentioned above, similarly, the preprocessing may be also related to the training target of the image processing model, that is, the preprocessing may be related to the application scenario of the image processing model. Taking the denoising as an exemplary application scenario, in some embodiments, the noise may be added by a noise adding algorithm. In some embodiments, the noise adding algorithm may include, but not limited to, a linear congruential algorithm, a Mersenne twister algorithm, a linear congruential algorithm with carry, or the like, or any combination thereof.

In some embodiments, a qualified image may be preprocessed to determine a plurality of sample images. For example, different levels of noise may be added to the qualified image, thereby determining the plurality of sample images. In some embodiments, the qualified image may be divided into a plurality of sub-images, and the plurality of sub-images may be preprocessed to determine the plurality of sample images. For example, different levels of noise may be added to each sub-image, thereby determining the plurality of sample images.

Figure 9A:
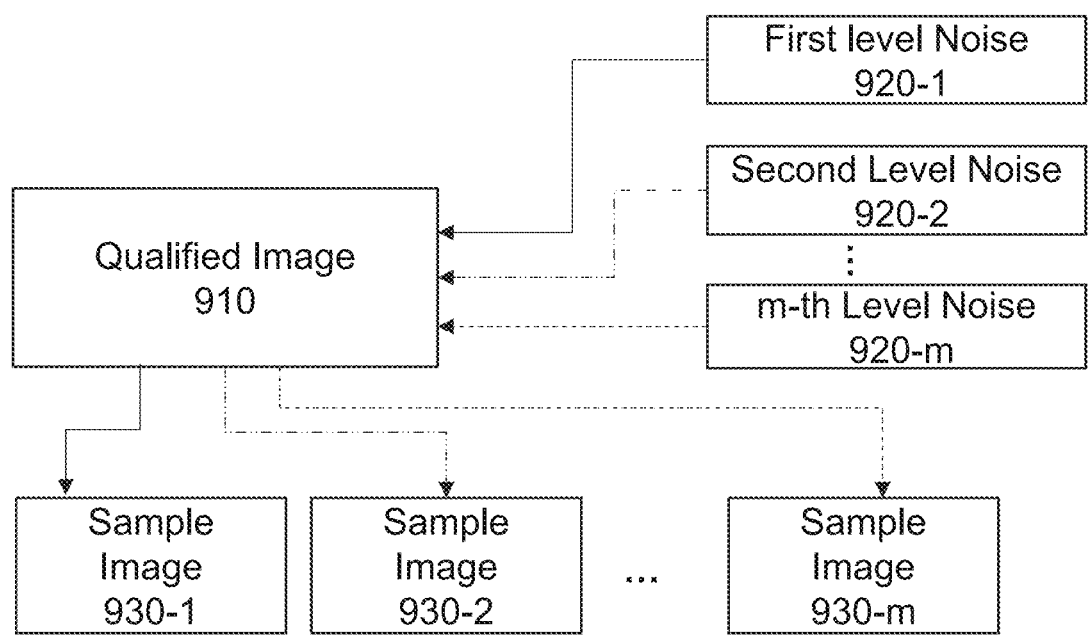
FIG. 9A and FIG. 9B are flowcharts illustrating exemplary processes for obtaining sample images by adding noises to a qualified image according to some embodiments of the present disclosure.
Figure 9B:
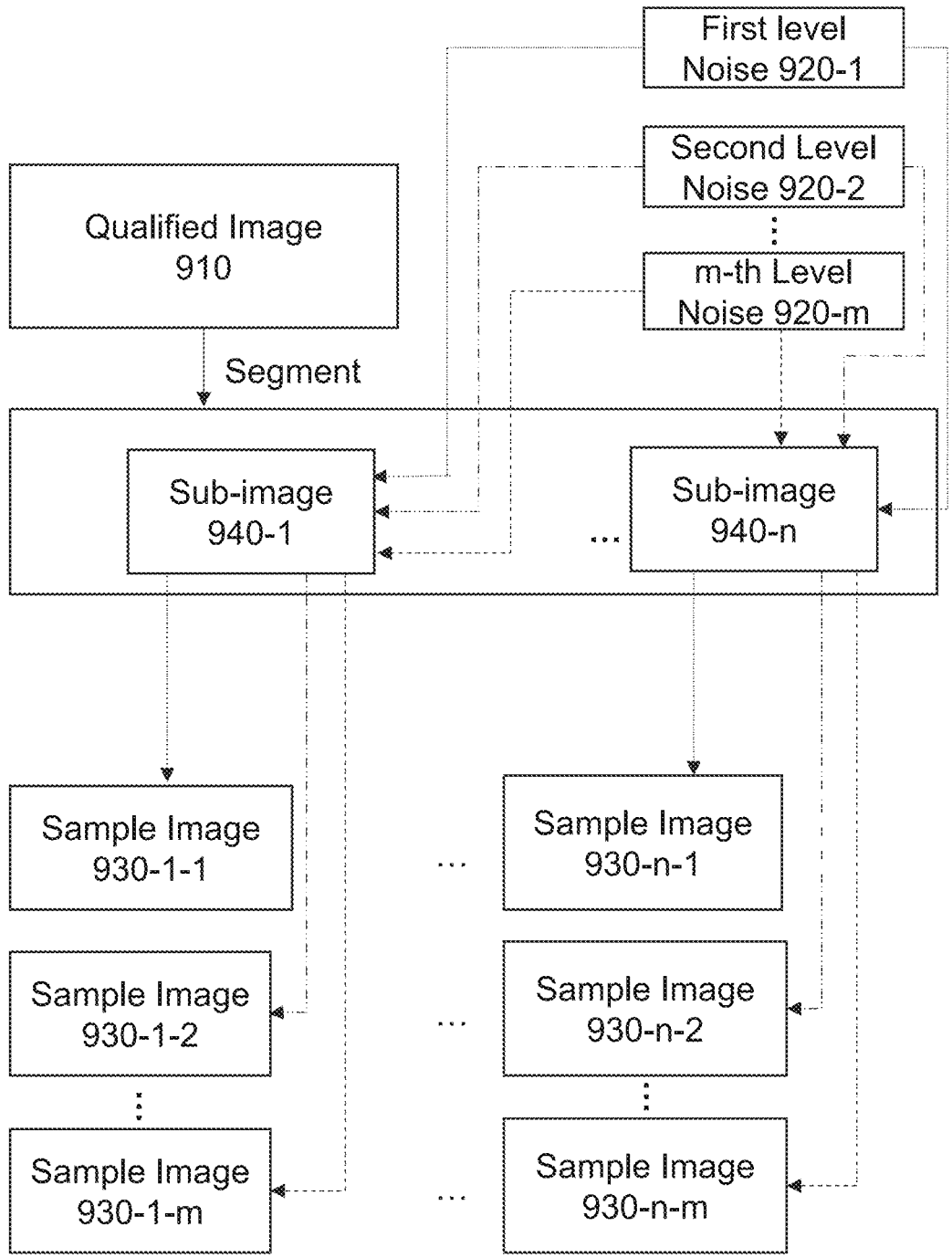

To describe the process for generating the sample images based on the qualified image more clearly and conveniently, the following FIG. 9A and FIG. 9B may be described as exemplary examples. FIGS. 9A and 9B are flowcharts illustrating exemplary processes for obtaining sample images by adding noises to a qualified image according to some embodiments of the present disclosure. For convenience, the process 900A and the process 900B shown in FIG. 9A and FIG. 9B take generating a plurality of sample images by adding noises to a qualified image as an example. It should be understood that the processes illustrated in FIGS. 9A and 9B can be also applicable to generating a plurality of sample images by adding artifacts, reducing resolution, or adding motion. The embodiments of the present disclosure are not intended to be limiting.

As shown in FIG. 9A, different levels of noise may be added to a qualified image 910, such as a first level noise 920-1, a second level noise 920-2, . . . , an m-th level noise 920-$m$, so as to determine sample images with different levels of noise, that is, a sample image 930-1, a sample image 930-2, . . . , and a sample image 930-$m$.

As shown in FIG. 9B, the qualified image 910 may be divided into a plurality of sub-images, that is, a sub-image 940-1, . . . , and a sub-image 940-$n$. Different levels of noise may be added to the plurality of sub-images to determine corresponding sample images with the different levels of noise. For example, the first level noise 920-1, the second level noise 920-2, . . . , and the m-th level noise 920-$m$ may be added to the sub-image 940-1, so as to determine a sample image 930-1-1, a sample image 930-1-2, . . . , and a sample image 930-1-$m$; . . . ; the first level noise 920-1, the second level noise 920-2, . . . , and the m-th level noise 920-$m$ may be added to the sub-image 940-$n$, so as to determine a sample image 930-$n$-1, a sample image 930-$n$-2, . . . , and a sample image 930-1-$m$.

In 830, for each of the plurality of training samples, the processing device 120$b$ (e.g., the acquisition module 450) may determine a corresponding qualified image as a standard image of the training sample.

For example, as shown in FIG. 9A, the qualified image 910 may be used as the standard image of the sample image 930-1, the sample image 930-2, . . . , and the sample image 930-$m$. As shown in FIG. 9B, the sub-image 940-1 (also referred to as "qualified sub-image") of the qualified image 910 may be used as the standard image of the sample image 930-1-1, the sample image 930-1-2, . . . , and the sample image 930-1-$m$.

Figure 10:
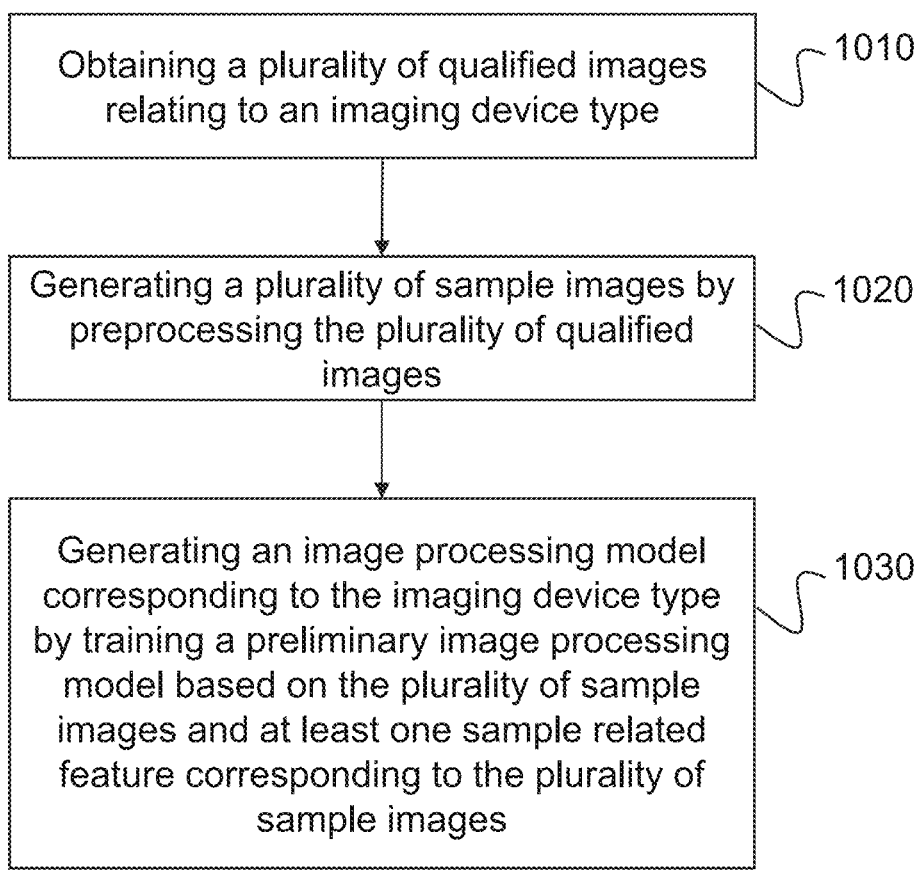
FIG. 10 is a flowchart illustrating an exemplary process for obtaining an image processing model corresponding to an imaging device type according to some embodiments of the present disclosure.

FIG. 10 is a flowchart illustrating an exemplary process for obtaining an image processing model corresponding to an imaging device type according to some embodiments of the present disclosure. In some embodiments, process 1000 may be executed online or offline by the processing device 120$b$ or other processing devices. In some embodiments, the process 1000 may be implemented as a set of instructions (e.g., an application) stored in a storage device (e.g., the storage device 150). The processing device 120$b$ may execute the set of instructions, and when executing the instructions, the processing device 120$b$ may be configured to perform the process 1000. The operations of the illustrated process presented below are intended to be illustrative. In some embodiments, the process 500 may be implemented according to one or more operations of the process 1000.

In 1010, the processing device 120$b$ (e.g., the acquisition module 450) may obtain a plurality of qualified images relating to an imaging device type.

As mentioned above, a qualified image may refer to an image whose image quality satisfies a preset requirement. Thus, the qualified image relating to the imaging device type may refer to a qualified image generated by an imaging device with the imaging device type. For example, for a CT device, the plurality of qualified images relating to the imaging device type may include a plurality of qualified CT images. As another example, for a PET device, the plurality of qualified images relating to the imaging device type may include a plurality of qualified PET images.

In some embodiments, the plurality of qualified images may be generated and stored in advance in a storage device (e.g., the storage device 150) disclosed elsewhere in the present disclosure. The processing device 120$b$ may acquire the plurality of qualified images directly from the storage device. In some embodiments, the processing device 120$b$ may generate the plurality of qualified images based on imaging data generated by the imaging device with the imaging device type.

In 1020, the processing device 120$b$ (e.g., the acquisition module 450) may generate a plurality of sample images by preprocessing the plurality of qualified images.

In some embodiments, the preprocessing may include segmentation, adding noise, adding artifacts, reducing resolution, adding motion, or the like, or any combination thereof.

In some embodiments, the processing device 120$b$ may segment the qualified image into a plurality of qualified sub-images using an image segmentation algorithm. The image segmentation algorithm may include, but not limited to, a threshold-based segmentation algorithm, an edge-based segmentation algorithm, an area-based segmentation algorithm, a cluster-based segmentation algorithm, an image segmentation algorithm based on a wavelet transform, an image segmentation algorithm based on mathematical morphology, an image segmentation algorithm based on an artificial neural network, or the like, or any combination thereof.

In some embodiments, the processing device 120$b$ may generate the plurality of sample images corresponding to a qualified image or a qualified sub-image by adding different interference information (e.g., different levels of noise, artifact, and/or motion) to the qualified image or the qualified sub-image. For example, the processing device 120$b$ may add different levels and/or different types of noise (e.g., a Gaussian noise, a pulse noise, a Rayleigh noise, an index distribution noise, a uniform distribution noise, a random noise) to the qualified image or the qualified sub-image. Similarly, the processing device 120$b$ may add different levels and/or different types of artifacts (e.g., a strip artifact, a cyclic artifact, a shadow artifact, a banding artifact, a windmill artifact, a streak artifact, a motion artifact) to the qualified image or the qualified sub-image. Similarly, the processing device 120$b$ may also add different levels and/or different types of motion to the qualified image or the qualified sub-image, and details are not repeated herein.

In some embodiments, the processing device 120b may adjust a resolution, a contrast, a grey, etc., of the qualified image or the sub-image to generate the plurality of sample images corresponding to the qualified image or the qualified sub-image. For example, the resolution of the qualified image or the qualified sub-image may be reduced in different levels.

In 1030, the processing device 120b (e.g., the training module 460) may generate an image processing model corresponding to the imaging device type by training a preliminary image processing model based on the plurality of sample images and at least one sample related feature corresponding to the plurality of sample images.

In some embodiments, the processing device 120b may obtain the preliminary image processing model described elsewhere in the present disclosure. The processing device 120b may acquire at least one sample quality feature corresponding to the plurality of sample images. The processing device 120b may generate the image processing model corresponding to the imaging device type by training the preliminary image processing model based on the plurality of sample images and the at least one sample related feature. A label of the sample images may be the corresponding qualified image or the qualified sub-image. The training of the image processing model corresponding to the imaging device type may be the same as or similar to the training process described in operation 720, and details are not repeated herein.

FIG. 11 is a flowchart illustrating an exemplary process for obtaining an image processing model corresponding to a subject type according to some embodiments of the present disclosure. In some embodiments, process 1100 may be executed online or offline by the processing device 120b or other processing devices. In some embodiments, the process 1100 may be implemented as a set of instructions (e.g., an application) stored in a storage device (e.g., the storage device 150). The processing device 120b may execute the set of instructions, and when executing the instructions, the processing device 120b may be configured to perform the process 1100. The operations of the illustrated process presented below are intended to be illustrative. In some embodiments, the process 500 may be implemented according to one or more operations of the process 1100.

In 1110, the processing device 120b (e.g., the acquisition module 450) may obtain a plurality of qualified images relating to a subject type.

As mentioned above, the qualified image may refer to an image whose image quality satisfies a preset requirement. Thus, the qualified image relating to the subject type may refer to a qualified image including the subject type. For example, for the subject type "chest," the plurality of qualified images relating to the subject type may include a plurality of qualified chest images. As another example, for the subject type "head," the plurality of qualified images relating to the subject type may include a plurality of qualified head images.

In some embodiments, the plurality of qualified images may be generated and stored in advance in a storage device (e.g., the storage device 150) disclosed elsewhere in the present disclosure. The processing device 120b may acquire the plurality of qualified images directly from the storage device. In some embodiments, the processing device 120b may generate the plurality of qualified images based on imaging data relating to the subject type.

In 1120, the processing device 120b (e.g., the acquisition module 450) may generate a plurality of sample images by preprocessing the plurality of qualified images.

In some embodiments, the preprocessing may include segmentation, adding noise, adding artifact, or the like, or any combination thereof. More descriptions regarding operation 1120 may be found in operation 1020 and the descriptions thereof, which are not repeated herein.

In 1130, the processing device 120b (e.g., the training module 460) may generate an image processing model corresponding to the subject type by training a preliminary image processing model based on the plurality of sample images and a plurality of sample quality features corresponding to the plurality of sample images.

In some embodiments, the processing device 120b may acquire the preliminary image processing model described elsewhere in the present disclosure. The processing device 120b may acquire at least one sample related feature corresponding to the plurality of sample images. The processing device 120b may generate the image processing model corresponding to the subject type by training the preliminary image processing model based on the plurality of sample images and the at least one sample related feature. A label of the sample images may be the corresponding qualified image or qualified sub-image. The training of the image processing model corresponding to the subject type may be the same as or similar to the training process described in operation 720, and details are not repeated herein.

Figure 12:
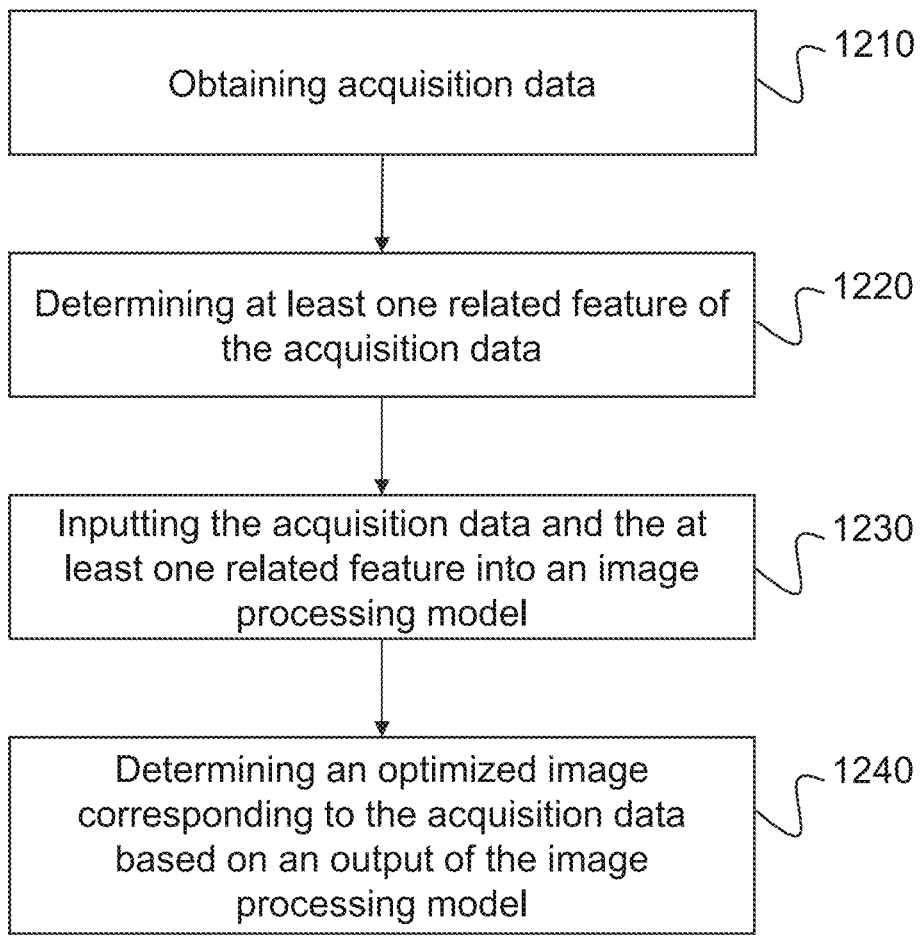
FIG. 12 is a flowchart illustrating another exemplary process for image quality optimization according to some embodiments of the present disclosure.

FIG. 12 is a flowchart illustrating an exemplary process for image quality optimization according to some embodiments of the present disclosure. In some embodiments, process 1200 may be executed by the processing device 120a or other processing devices. In some embodiments, the process 1200 may be implemented as a set of instructions (e.g., an application) stored in a storage device (e.g., the storage device 150, the storage 220, and/or the storage 390). The processing device 120a (e.g., the processor 210, the CPU 340, and/or one or more modules illustrated in FIG. 4A) may execute the set of instructions, and when executing the instructions, the processing device 120a or the other processing devices may be configured to perform the process 1200. The operations of the illustrated process presented below are intended to be illustrative. In some embodiments, the process 1200 may be accomplished with one or more additional operations not described and/or without one or more of the operations discussed. Additionally, the order of the operations of the process 1200 illustrated in FIG. 12 and the content described below are not intended to be limiting.

In 1210, the processing device 120a (e.g., the acquisition module 410) may obtain acquisition data to be processed.

More descriptions regarding the acquisition data may be found in operation 610 and the descriptions thereof, which are not repeated herein. More descriptions regarding operation 1210 may be found in operation 510 and the descriptions thereof, which are not repeated herein.

In 1220, the processing device 120a (e.g., the determination module 420) may determine at least one related feature of the acquisition data.

In some embodiments, the at least one related feature of the acquisition data may include at least one of an acquisition parameter feature relating to the acquisition data, an imaging parameter feature relating to the acquisition data, an imaging subject feature of an imaging subject, or a quality feature of the acquisition data. More descriptions regarding operation 1220 may be found in operation 520 and the descriptions thereof, which are not repeated herein.

In 1230, the processing device 120*a* (e.g., the inputting module 430) may input the acquisition data and the at least one related feature into an image processing model.

More descriptions regarding operation 1230 may be found in operation 530 and the descriptions thereof, which are not repeated herein.

In 1240, the processing device 120*a* (e.g., the optimization module 440) may determine an optimized image corresponding to the acquisition data based on an output of the image processing model.

More descriptions regarding operation 1240 may be found in operation 540 and the descriptions thereof, which are not repeated herein.

Figure 13A:
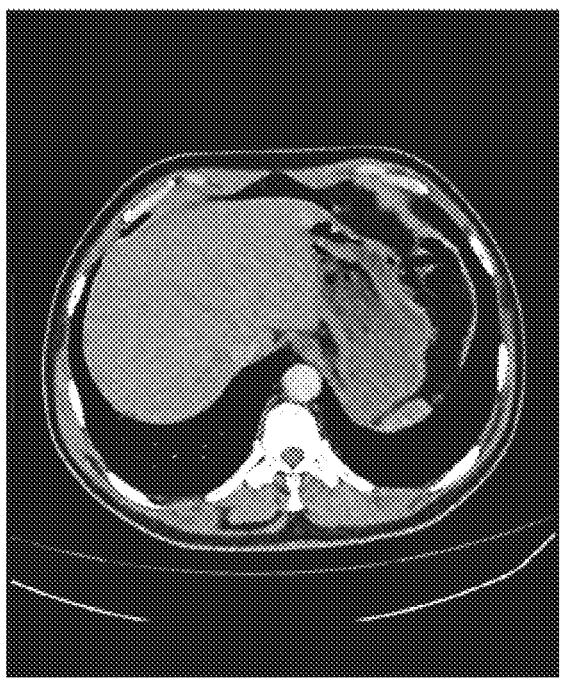
FIG. 13A and FIG. 13B are image results indicating an effect comparison between the optimization method according to some embodiments of the present disclosure and other methods.
Figure 13B:
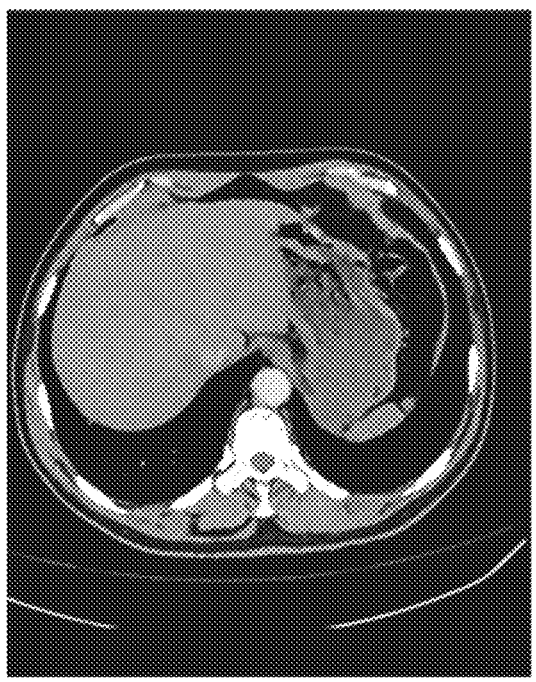

FIGS. 13A and 13B are image results indicating an effect comparison between the optimization method according to some embodiments of the present disclosure and other methods.

FIG. 13A is an optimized image of a liver, which is optimized by an image processing model that is trained without at least one related feature. FIG. 13B is an optimized image of a liver, which is optimized by an image processing model that is trained with the at least one related feature. According to FIG. 13A and FIG. 13B, it can be seen that there is noise in the liver in the optimized image of FIG. 13A, indicating a poor noise reduction effect, which may affect the subsequent image analysis and affect normal diagnosis. However, the optimized image in FIG. 13B can better reconstruct a structure of the liver without noise left, which accordingly can provide accurate information for the subsequent diagnosis. That is, according to methods disclosed in the embodiments of the present disclosure, the image processing model has better learning capabilities for noise distribution, better processing capabilities for noise, and a better noise reduction effect.

The embodiments of the present disclosure may also provide an image quality optimization device including a processor and a memory. The memory may be configured to store instructions, and the processor may be configured to execute the instructions to implement operations of an image quality optimization method described anywhere in the present disclosure.

The embodiments of the present disclosure may also provide a computer-readable storage medium storing at least one set of instructions. When executed by a processor, the at least one set of instructions may direct the processor to execute operations corresponding to an image quality optimization method described anywhere in the present disclosure.

The beneficial effects of the present disclosure may include, but not limited to, by introducing multiple dimensions of related features (e.g., an acquisition parameter feature, an imaging parameter feature, an imaging subject feature, a quality feature) of an image into a training process of a model, the image processing model can better learn information of the multiple dimensions of the image, thereby better achieving the image optimization purpose. It should be noted that different embodiments may have different beneficial effects. In different embodiments, the possible beneficial effects may be any one or a combination of the above, or may be any other beneficial effects that may be obtained.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (e.g., through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for image quality optimization, comprising:
   obtaining an image to be processed;
   determining at least one related feature of the image, the at least one related feature including at least one of an acquisition parameter feature relating to the image, an imaging parameter feature relating to the image, an imaging subject feature of an imaging subject, or a quality feature of the image;
   inputting the image and the at least one related feature into an image processing model; and
   determining an optimized image corresponding to the image based on an output of the image processing model.

2. The method of claim 1, wherein the acquisition parameter feature includes at least one of:
   a voltage parameter, a current parameter, a filtering parameter of a scanning signal, a size of a detector, a response character of the detector to a signal, a sensitive character of the detector to signal motion, or an intensity value of a noise generated by the detector.

3. The method of claim 1, wherein the imaging parameter feature includes at least one of:
   a count of pixels, a pixel pitch, a reconstruction thickness, a reconstruction interval, or a convolution kernel parameter.

4. The method of claim 1, wherein the imaging subject feature includes at least one of:
   a stature of the imaging subject, an age of the imaging subject, a gender of the imaging subject, a body density of the imaging subject, an attenuation distribution of the imaging subject to X-rays, a density of an imaging target of the imaging subject, an attenuation distribution of the imaging target to X-rays, a density of each of a plurality of scanning layers of the imaging subject, an attenuation distribution of each of the plurality of scanning layers of the imaging subject to X-rays, a density of each of a plurality of scanning layers of the imaging target, or an attenuation density of each of the plurality of scanning layers of the imaging target to X-rays.

5. The method of claim 1, wherein the quality feature includes at least one of a noise feature, an artifact feature, a motion feature, a grayscale feature, a resolution, or a contrast of the image.

6. The method of claim 5, wherein
   the quality feature includes the noise feature of the image,
   the method further comprises determining the noise feature of the image, comprising:
      obtaining a preliminary noise feature of acquisition data corresponding to the image; and
      generating the noise feature of the image by performing an image reconstruction based on the preliminary noise feature and the acquisition data.

7. The method of claim 6, wherein the obtaining a preliminary noise feature of acquisition data corresponding to the image comprises:
   obtaining at least one acquisition signal intensity corresponding to the acquisition data;

determining at least one noise amplitude corresponding to the at least one acquisition signal intensity; and determining the preliminary noise feature of the acquisition data based on the at least one noise amplitude.

8. The method of claim 1, wherein the at least one related feature includes the quality feature, the method further comprises determining the quality feature, comprising:

inputting at least one of the acquisition parameter feature, the imaging parameter feature, or the imaging subject feature into a feature processing model; and determining the quality feature of the image based on an output of the feature processing model.

9. The method of claim 1, further comprising:

selecting the image processing model based on at least one of the acquisition parameter feature, the imaging parameter feature, or the imaging subject feature.

10. The method of claim 1, wherein the image processing model is determined through a training process, the training process comprising:

obtaining a plurality of training samples and a plurality of standard images corresponding to the plurality of training samples respectively, wherein each of the plurality of training samples includes a sample image and at least one sample related feature of the sample image, the at least one sample related feature including at least one of a sample acquisition parameter feature relating to the sample image, a sample imaging parameter feature relating to the sample image, a sample imaging subject feature, or a sample quality feature of the sample image; and determining the image processing model by training a preliminary image processing model based on the plurality of training samples and the plurality of standard images.

11. The method of claim 10, wherein a loss function of the image processing model is positively correlated with a quality weight, the quality weight being determined based on the sample quality feature.

12. A method for image quality optimization, comprising:

obtaining acquisition data to be processed;

determining at least one related feature of the acquisition data, the at least one related feature including at least one of an acquisition parameter feature relating to the acquisition data, an imaging subject feature of an imaging subject, or a quality feature of the acquisition data;

inputting the acquisition data and the at least one related feature into an image processing model; and determining optimized image data corresponding to the acquisition data based on an output of the image processing model.

13. A system for image quality optimization, comprising:

at least one storage device storing executable instructions; and at least one processor in communication with the at least one storage device, wherein when executing the executable instructions, the at least one processor is configured to cause the system to perform operations including:

obtaining an image to be processed;

determining at least one related feature of the image, the at least one related feature including at least one of an acquisition parameter feature relating to the image, an imaging parameter feature relating to the image, an imaging subject feature of an imaging subject, or a quality feature of the image;

inputting the image and the at least one related feature into an image processing model; and determining an optimized image corresponding to the image based on an output of the image processing model.

14. The system of claim 13, wherein the acquisition parameter feature includes at least one of:

a voltage parameter, a current parameter, a filtering parameter of a scanning signal, a size of a detector, a response character of the detector to a signal, a sensitive character of the detector to signal motion, or an intensity value of a noise generated by the detector.

15. The system of claim 13, wherein the imaging parameter feature includes at least one of:

a count of pixels, a pixel pitch, a reconstruction thickness, a reconstruction interval, or a convolution kernel parameter.

16. The system of claim 13, wherein the imaging subject feature includes at least one of:

a stature of the imaging subject, an age of the imaging subject, a gender of the imaging subject, a body density of the imaging subject, an attenuation distribution of the imaging subject to X-rays, a density of an imaging target of the imaging subject, an attenuation distribution of the imaging target to X-rays, a density of each of a plurality of scanning layers of the imaging subject, an attenuation distribution of each of the plurality of scanning layers of the imaging subject to X-rays, a density of each of a plurality of scanning layers of the imaging target, or an attenuation density of each of the plurality of scanning layers of the imaging target to X-rays.

17. The system of claim 13, wherein the quality feature includes at least one of a noise feature, an artifact feature, a motion feature, a grayscale feature, a resolution, or a contrast of the image.

18. The system of claim 17, wherein the quality feature includes the noise feature of the image, the at least one processor is further configured to cause the system to perform operations including:

obtaining a preliminary noise feature of acquisition data corresponding to the image; and generating the noise feature of the image by performing an image reconstruction based on the preliminary noise feature and the acquisition data.

19. The system of claim 18, wherein the obtaining a preliminary noise feature of acquisition data corresponding to the image comprises:

obtaining at least one acquisition signal intensity corresponding to the acquisition data;

determining at least one noise amplitude corresponding to the at least one acquisition signal intensity; and determining the preliminary noise feature of the acquisition data based on the at least one noise amplitude.

20. The system of claim 13, wherein the at least one processor is further configured to cause the system to perform operations including:

selecting the image processing model based on at least one of the acquisition parameter feature, the imaging parameter feature, or the imaging subject feature.

* * * * *

UNITED STATES PATENT AND TRADEMARK OFFICE
CERTIFICATE OF CORRECTION

PATENT NO. : 12,141,965 B2
APPLICATION NO. : 17/446303
DATED : November 12, 2024
INVENTOR(S) : Yifu Mao et al.

Page 1 of 1

It is certified that error appears in the above-identified patent and that said Letters Patent is hereby corrected as shown below:

On the Title Page

In the Foreign Application Priority Data
Item (30), Line 2, "May 18, 2020 (CN) .............. PCT/CN2020/090862" should be added.

Signed and Sealed this
Twenty-first Day of January, 2025

Coke Morgan Stewart
*Acting Director of the United States Patent and Trademark Office*